United States Patent
Miyatake et al.

(10) Patent No.: US 11,603,515 B2
(45) Date of Patent: Mar. 14, 2023

(54) CELL CULTURE SUBSTRATE, CANCER CELL AGGREGATE AND METHOD FOR MANUFACTURING SAME USING SAID SUBSTRATE, AND DRUG SCREENING METHOD USING SAID CANCER CELL AGGREGATE

(71) Applicant: NATIONAL UNIVERSITY CORPORATION HOKKAIDO UNIVERSITY, Sapporo (JP)

(72) Inventors: Yukiko Miyatake, Sapporo (JP); Kaori Shigetomi, Sapporo (JP); Takaharu Okajima, Sapporo (JP); Masanori Kasahara, Sapporo (JP)

(73) Assignee: NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 529 days.

(21) Appl. No.: 16/499,649

(22) PCT Filed: Apr. 2, 2018

(86) PCT No.: PCT/JP2018/014119
§ 371 (c)(1),
(2) Date: Sep. 30, 2019

(87) PCT Pub. No.: WO2018/182044
PCT Pub. Date: Oct. 4, 2018

(65) Prior Publication Data
US 2020/0063083 A1 Feb. 27, 2020

(30) Foreign Application Priority Data
Mar. 31, 2017 (JP) .............................. JP2017-072512

(51) Int. Cl.
*C12M 1/00* (2006.01)
*C12M 1/12* (2006.01)
*C12N 5/09* (2010.01)
*G01N 33/50* (2006.01)

(52) U.S. Cl.
CPC ............ *C12M 25/06* (2013.01); *C12N 5/0693* (2013.01); *G01N 33/5011* (2013.01); *C12N 2533/30* (2013.01)

(58) Field of Classification Search
CPC .................................................. C12N 2533/30
See application file for complete search history.

(56) References Cited

U.S. PATENT DOCUMENTS

| | | |
|---|---|---|
| 2009/0170190 A1 | 7/2009 | Nishi et al. |
| 2009/0246872 A1 | 10/2009 | Ozawa et al. |
| 2014/0227784 A1 | 8/2014 | Ejiri et al. |
| 2016/0160175 A1 | 6/2016 | Itchoda et al. |

FOREIGN PATENT DOCUMENTS

| | | |
|---|---|---|
| JP | 2007-209218 A | 8/2007 |
| JP | 2013-208086 A | 10/2013 |
| JP | 2016-136848 A | 8/2016 |
| WO | WO 2007/097120 A1 | 8/2007 |
| WO | WO 2007/097121 A1 | 8/2007 |
| WO | WO 2007/105418 A1 | 9/2007 |
| WO | WO 2010/032846 A1 | 3/2010 |
| WO | WO 2010/047132 A1 | 4/2010 |
| WO | WO 2013/042360 A1 | 3/2012 |

OTHER PUBLICATIONS

Tan et al., Tissue Engineering, 2004, 10(5/6):865-872.*
Matsuno et al., J. Nanosci. Nanotechnol,, 2009, 9(1):358-365.*
English translation of the International Preliminary Report on Patentability dated Oct. 3, 2019, in PCT/JP2018/014119, 6 pages.
International Search Report dated Jul. 24, 2018, in PCT/JP2018/014119, 2 pages.
Zheng, X. et al., "EMT Program is Dispensable for Metastasis but Induces Chemoresistance in Pancreatic Cancer", Nature, vol. 527, No. 7579, Nov. 26, 2015, 31 pages.
Ohsawa.S. et al., "Inhibition of cancer inherent in epithelium in which cell competition is driven", Experimental Medicine, vol. 29, No. 9, 2011, pp. 1374-1380 (with unedited computer generated English translation).
Overholtzer, M. et al., "A Nonapoptotic Cell Death Process, Entosis, that Occurs by Cell-in-Cell Invasion", Cell, vol. 131, Nov. 30, 2007, pp. 966-979.
Miyatake, Y. et al., "Visualising the dynamics of live pancreatic microtumours self-organised through cell-in-cell invasion", Scientific Reports, vol. 8, No. 14054, 2018, 13 pages.

(Continued)

*Primary Examiner* — Bin Shen
(74) *Attorney, Agent, or Firm* — Oblon, McClelland, Maier & Neustadt, L.L.P.

(57) ABSTRACT

[Problem] An object of the present invention is to produce cancer cell clusters with intrinsic biological properties as cancer tissues, such as morphological polarity and tissue motion polarity, in vitro.
[Solution] The present invention relates to a cell culture substrate including a base material and a biocompatible polymer layer, the substrate including a plurality of rough sections on the surface of the substrate, wherein the rough sections are not covered with the biocompatible polymer layer, have a predetermined surface structure with a predetermined shape, and are disposed at predetermined intervals. With the present invention, it is possible to obtain a live cancer cell aggregate having morphological polarity and tissue motion polarity similar to that observed in vivo, by a very easy operation of culturing cancer cells on a cell culture substrate having a predetermined structure, thereby performing live imaging of microtumors in vitro is enabled, which has been conventionally impossible. Moreover, since such a cancer cell aggregate is considered to reproduce a series of flow of development, proliferation, infiltration, metastasis, and recurrence of cancer in vivo, the cancer cell aggregate can be utilized as a research tool in cancer research, or for screening for an anticancer drug.

12 Claims, 44 Drawing Sheets

(56) References Cited

OTHER PUBLICATIONS

Japanese Office Action dated Mar. 22, 2022, in Japanese Patent Application No. 2019-509439 (with English Translation).
Udesh Dhawan et al., Nanochips of Tantalum Oxide Nanodots as artificial-microenvironments for monitoring Ovarian cancer progressiveness, Scientific Reports, www.nature.com/scientificreports, pp. 1-12, Published Aug. 18, 2016.
Muhymin Islam et al., Nanotextured polymer substrates show enhanced cancer cell isolation and cell culture, IOP Publishing, Nanotechnology 26 (2015) 225101, pp. 1-9.
Daniel J T Kyle et al., Fabrication and modelling of fractal, biomimetic, micro and nano-topographical surfaces, IOP Publishing, Bioinspiration & Biomimetics, pp. 1-15, Published Jul. 25, 2016.
Yukiko Miyatake et al., Protective Roles of Epithelial Cells in the Survival of Adult T-Cell Leukemia/Lymphoma Cells, The American Journal of Pathology, vol. 182, No. 5, May 2013, pp. 1832-1842.
Yukiko Miyatake et al., Anchorage-dependent multicellular aggregate formation induces CD44 high cancer stem cell-like ATL cells in an NF-kappa B- and vimentin-dependent manner, Hokkaido University Collection of Scholarly and Academic Papers, Feb. 1, 2015, 1-37.
E. Stratakis et al., Biomimetic micro/nanostructured functional surfaces for microfluidic and tissue engineering applications, Biomicrofludics 5, 013411 (2011), pp. 1-31.

* cited by examiner

MIA PaCa-2 cells cultured on micro-nano base material

Before wash · After wash

PCI-55 · MIA PaCa-2

CELL CULTURE SUBSTRATE, CANCER CELL AGGREGATE AND METHOD FOR MANUFACTURING SAME USING SAID SUBSTRATE, AND DRUG SCREENING METHOD USING SAID CANCER CELL AGGREGATE

CROSS-REFERENCE TO RELATED APPLICATIONS

The present application is a 35 U.S.C. § 371 national stage patent application of International patent application PCT/JP2018/014119, filed on Apr. 2, 2018, which is based on and claims the benefits of priority to Japanese Application No. 2017-072512, filed on Mar. 31, 2017. The entire contents of all of the above applications are incorporated herein by reference.

FIELD

The present invention relates to a cell culture substrate having a predetermined structure, a cancer cell aggregate and a method for producing the same using the substrate, and a method for screening a drug for preventing and/or treating cancer using the cancer cell aggregate.

BACKGROUND

Cancer is a disease that has yet to be completely conquered. Increases in cost of developing new drugs and in the number of cancer patients in a super-aging society increase health expenditure and place a heavy burden on the national budget. Under such circumstances, development of effective and inexpensive next-generation cancer treatment drugs is an urgent issue.

In the study of cancer as a disease, biological properties of cancer in the cellular level have been elucidated. However, despite its importance, biological dynamic properties in the cancer tissue level, which is a collection of cancer cells, have not attracted attention and remain mostly unclear due to a lack in observation techniques. Consequently, investigation of cancer tissues in vitro in basic molecular physiology, and particularly, elucidation of biological dynamic properties of cancer tissues are expected to have significant implications on the development of next-generation cancer treatment drugs.

In the major molecular and physiological investigations in the cancer tissue level that have been conventionally carried out in cancer research, a biological tissue sample removed from a living body is fixed, observed pathologically and diagnostically, and estimated. On the other hand, a technique for in vitro live imaging of cancer cell clusters from a living body has not yet been developed due to technical difficulties. Thus, basic cancer research, new anticancer drug development, and the like have been carried out with almost no consideration paid to the pathophysiological dynamics of cancer tissues.

It is known that many epithelial cancer cells require epithelial-mesenchymal transition (EMT) for infiltration and metastasis. It is considered that epithelial cancer cells lose the epithelial phenotype by the EMT, and cause infiltration and metastasis by acquiring a mesenchymal phenotype such as motility and infiltrative capacity. However, a recent research has clarified that in pancreatic ductal adenocarcinoma cells, infiltration and metastasis without EMT occur (Non Patent Literature 1). A collective cell migration has attracted attention as a new cancer infiltration and metastasis mechanism without EMT, and a demand for techniques for in vitro observation of cancer cell clusters from a living body has been increasing.

In vitro, what is called three-dimensional cell culture, which is not conventional two-dimensional monolayer cell culture, but forms a three-dimensional cell mass using a culture substrate having a special structure, has been reported to more closely mimic the vivo environment (for example, Patent Literatures 1 and 2, and the like). However, most of the cell masses formed by the three-dimensional cell culture is spheroid (spheroidal cancer cell mass), which does not exhibit active motion polarity or morphological polarity and exhibits expansive proliferation. Thus, the cell mass is far from properly reflecting a cancer cell cluster in vivo, which exhibits infiltrative proliferation as a characteristic of a malignant tumor.

Moreover, for normal epithelial cells to survive and proliferate, the cells need to adhere to an anchorage such as an extracellular matrix. Epithelial cells that have failed to suitably adhere to an anchorage go into apoptosis called anoikis and will die. On the other hand, it is known that epithelial cancer cells that have undergone EMT escape cell death by acquiring anoikis resistance, flow inside the vascular, and metastasize from the primary lesion to other tissues.

The anoikis resistance in the epithelial cancer cells relates to tendency of cancer to infiltrate and metastasize. Thus, it is meaningful to determine the anoikis resistance in epithelial cancer cells. However, the epithelial cancer cells adhere to a cell culture substrate conventionally used for culturing epithelial cancer cells, regardless of the anoikis resistance. Thus, it has been difficult to evaluate the anoikis resistance in epithelial cancer cells in vitro.

CITATION LIST

Non Patent Literature

Non Patent Literature 1: Zheng et al., Nature, 2015, 527 (7579): 525-530.

Patent Literature

Patent Literature 1: WO2007/097120
Patent Literature 2: WO2013/042360

SUMMARY

Technical Problem

An object of the present invention is to produce cancer cell clusters with intrinsic biological properties as cancer tissues, such as morphological polarity and tissue motion polarity, in vitro.

Solution to Problem

The present inventors have found out that when cancer cells are cultured using a cell culture substrate in which a rough section with a predetermined shape and surface roughness is disposed at a predetermined interval, the cancer cells form a cell mass having morphological polarity and tissue motion polarity that can be observed in a cancer cell cluster in vivo, using an uneven structure on the rough section surface as an anchorage. The present inventors have then completed the following invention.

(1) A cell culture substrate including a base material and a biocompatible polymer layer, the substrate including a plurality of rough sections not covered with the biocompatible polymer layer on the surface of the substrate, in which the shape of each of the rough sections is a spot with a diameter ranging from 20 µm to 100 µm, or a groove with a width ranging from 3 µm to 30 µm, when the shape of the rough section is a groove, an end part of the rough section is optionally connected to another rough section, a distance between two adjacent rough sections is at least 10 µm or more, and the rough section has an uneven structure with a height ranging from 20 nm to 200 nm on the surface.
(2) The cell culture substrate according to (1), in which the rough section has a developed interfacial area ratio (Sdr) of 0.002 or more.
(3) The cell culture substrate according to (1) or (2), in which the distance between the two adjacent rough sections ranges from 10 to 1,200 µm.
(4) The cell culture substrate according to any one of (1) to (3), in which the rough section surface has an arithmetic mean roughness (Ra) of 4 nm or more, a maximum height roughness (Rz) of 30 nm or more, and/or an arithmetic mean peak curvature (Spc) of 300 or more.
(5) The cell culture substrate according to any one of (1) to (4), in which the biocompatible polymer is an amphiphilic polymer that inhibits non-specific adsorption to a biological material.
(6) The cell culture substrate according to any one of (1) to (5), in which the biocompatible polymer is 2-methacryloyloxyethyl phosphorylcholine.
(7) A cancer cell aggregate that has the following characteristics (a) to (e), that is formed of adherent cancer cells, and that is isolated and alive:
(a) having cell-in-cell structure,
(b) having non-spheroidal morphology,
(c) having membranous expression of α-tubulin on surface,
(d) having morphological polarity, and
(e) having tissue motion polarity.
(8) The cancer cell aggregate according to (7), further having at least one of the following characteristics (f) to (k):
(f) having capability to reversibly release and incorporate live cancer cells,
(g) having cilia on surface,
(h) exhibiting filipodia or lamellipodia morphology,
(i) having capability to incorporate dead cells,
(j) having cell debris suction force, and
(k) having phosphatidylserine-positive surface.
(9) A complex consisting of a cell culture substrate having a three-dimensional structure and the cancer cell aggregate according to claim 7 or 8 attached to the substrate.
(10) A method for producing the cancer cell aggregate according to (7) or (8), the method including a step of culturing adherent cancer cells using the cell culture substrate according to any one of (1) to (6).
(11) A method for producing the complex according to (9), the method including a step of culturing adherent cancer cells using the cell culture substrate according to any one of (1) to (6).
(12) A method for screening a drug for preventing and/or treating cancer, the method including:
a step of making the cancer cell aggregate according to (7) or (8) coexist with a test substance;
a step of observing the above cancer cell aggregate for at least one of the following characteristics:
(a) having cell-in-cell structure,
(b) having non-spheroidal morphology,
(c) having membranous expression of α-tubulin on surface,
(d) having morphological polarity,
(e) having tissue motion polarity,
(f) having capability to reversibly release and incorporate live cancer cells,
(g) having cilia on surface,
(h) exhibiting filipodia or lamellipodia morphology,
(i) having capability to incorporate dead cells,
(j) having cell debris suction force, and
(k) having phosphatidylserine-positive surface, and making a comparison with those of the cancer cell aggregate according to (7) or (8) that is not made to coexist with the test substance; and
a step of determining that the test substance has an anticancer activity when attenuation or loss of the above characteristics is more strongly observed in the coexistence with the test substance.
(13) A method for screening a drug for preventing and/or treating cancer, the method including:
a step of making the cancer cell aggregate according to (7) or (8) coexist with a test substance;
a step of measuring a length or size of the above cancer cell aggregate or pseudopodium thereof and making a comparison with that of the cancer cell aggregate according to (7) or (8) that is not made to coexist with the test substance; and
a step of determining that the test substance has an anticancer activity when the cancer cell aggregate or the pseudopodium becomes shorter or smaller in the coexistence with the test substance.
(14) The method according to (12) or (13), in which the drug is a drug for inhibiting infiltration and/or metastasis of cancer.
(15) The method according to (12) or (13), in which the drug is a drug for inhibiting and/or releasing immune evasion mechanism in cancer.
(16) A method for determining anoikis resistance in epithelial cancer cells, the method including:
a step of culturing test epithelial cancer cells using the cell culture substrate according to any one of (1) to (6); and
a step of determining that the epithetical cancer cells have anoikis resistance when the epithetical cancer cells have proliferated without adhering to the cell culture substrate.

Advantageous Effects of Invention

With the present invention, it is possible to obtain a live cancer cell aggregate having morphological polarity and tissue motion polarity similar to that observed in vivo, by an easy operation of culturing cancer cells on a cell culture substrate having a predetermined structure. Consequently, it is possible to perform live imaging of microtumors in vitro, which has been conventionally impossible. Moreover, such a cancer cell aggregate is considered to represent in vitro a series of flow of development, proliferation, infiltration, metastasis, and recurrence of cancer in vivo. Consequently, the cancer cell aggregate can be utilized as a research tool in cancer research, or for chemical compound screening in new anticancer drug development.

DESCRIPTION OF EMBODIMENTS

Figure 1:
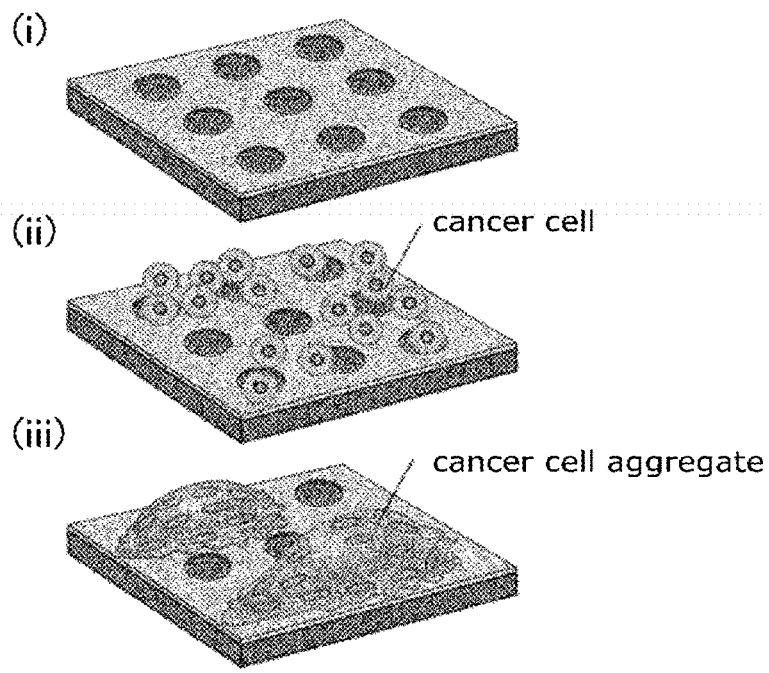
FIG. 1 includes image diagrams of the formation of a cancer cell aggregate (hereinafter, also referred to as a "microtumor") of a second aspect of the present invention, using a cell culture substrate of a first aspect of the present invention.

FIG. 1 schematically illustrates an example of a cell culture substrate according to a first aspect of the present invention, and a cancer cell aggregate according to a second aspect of the present invention formed on the substrate. The cell culture substrate has a plurality of rough sections with predetermined characteristics, and provides an uneven structure on the rough section surface to cells as an anchorage. Cancer cells seeded on the cell culture substrate form a cancer cell aggregate according to the second aspect of the present invention so that the cancer cell aggregate stretches across the rough sections.

1. Cell Culture Substrate

The first aspect of the present invention relates to a cell culture substrate that has a base material and a biocompatible polymer layer. The substrate has the rough sections not covered with the biocompatible polymer layer on the substrate surface. The shape of each of the rough sections is either a spot with a diameter ranging from 20 μm to 100 μm, or a groove with a width ranging from 3 μm to 30 μm. When the shape of the rough section is a groove, the end part of the rough section may be connected to the other rough section. The distance between the two adjacent rough sections is at least 10 μm or more, and the rough section has an uneven structure with a height ranging from 20 nm to 200 nm on the surface.

The cell culture substrate in the first aspect has the base material and the biocompatible polymer layer. The "base material" is a plate substance formed from a material generally used as a substrate for culturing cells, and for example, is a material on which unevenness in nanometers can be formed by a surface micromachining technique such as plasma processing or etching processing. In the present invention, a preferable example of the base material is a plate substance formed from a material such as silicon, glass, or plastic. In the first aspect of the present invention, a preferable base material is a glass base material.

The size and thickness of the base material are not particularly limited, as long as the size and thickness are about the same as those normally used for a base material for culturing cells.

The "biocompatible polymer" is a high molecular compound that does not have a harmful influence on cells. The biocompatible polymer in the present invention is not limited as long as the biocompatible polymer can inhibit a biological material such as cells from nonspecifically adsorbing to the cell culture substrate. The biocompatible polymer in the present invention is preferably an amphiphilic polymer that does not have non-specific adsorption properties to cells, such as dimethyl polysiloxane (PDMS), or polyethylene glycol (PEG), oligoethylene glycol (OED); or 2-methacryloyloxyethyl phosphorylcholine (hereinafter, also referred to as MPC). MPC is particularly preferable. The thickness of the biocompatible polymer layer is not particularly limited, as long as the thickness is about the same as that used for coating cell culture substrates in general.

In the cell culture substrate in the first aspect, the rough sections not covered with the biocompatible polymer layer are provided on the substrate surface. The "rough section" is a portion on the cell culture substrate surface where the biocompatible polymer layer is not present, the substance under the biocompatible polymer layer is exposed, and the surface has an uneven structure. For example, when the biocompatible polymer is directly brought into contact with the top of the base material, the rough section is a portion where the base material is exposed, and the surface of which has an uneven structure.

The shape of the rough section in the cell culture substrate in the first aspect is either a spot with a diameter ranging from 20 μm to 100 μm, or a groove with a width ranging from 3 μm to 30 μm. When the shape of the rough section is a groove, the end part of the rough section may be connected to the other rough section. Moreover, the distance between the two adjacent rough sections is at least 10 μm or more, and the rough section surface has an uneven structure with a height ranging from 20 nm to 200 nm. Here, the "rough section surface" represents the surface of a portion where the substance under the biocompatible polymer layer is exposed.

When the rough section is a spot, the contour is not particularly limited. However, the contour is preferably a polygon of a tetragon or more, a semicircle, an oval, or a circle. The diameter of the spot ranges from 20 μm to 150 μm, preferably from 20 μm to 100 μm, more preferably from 20 μm to 80 μm, and furthermore preferably from 30 μm to 80 μm. Here, the diameter is an arithmetic mean value of the size or width of the spot in the surface direction. In other words, when the contour of the spot is a polygon, the diameter is an arithmetic mean value of the length of diagonal lines from each apex. When the contour is a circle, the diameter is the diameter of the circle. When the contour is an oval or has the similar shape, the diameter is an arithmetic mean value of the long diameter and the short diameter. Consequently, the term diameter does not mean to limit the shape of a spot to a circle.

When the rough section is a groove, the width of the groove ranges from 3 μm to 30 μm, and preferably from 5 μm to 20 μm. The length of the groove may be 100 μm or more, and the maximum length is not particularly limited.

In terms of forming a cancer cell aggregate more efficiently, the length of the groove is desirably 150 μm or more, preferably 200 μm or more, and more preferably 400 μm or more. The shape of the groove may be a straight line or a curve, and may also be a combination of a straight line and a curve. Moreover, a part of the groove may be intersected with the other groove. Furthermore, the end of the groove may be connected to the end of the other groove.

In a below-described method for screening a drug for preventing and/or treating cancer in which the length or size of the cancer cell aggregate or the pseudopodium is used as an index, when a cell culture substrate in which the shape of the rough section is a groove is used, in order to extend the pseudopodium of the cancer cell aggregate efficiently in particular, it is preferable that the groove have a straight line portion of 20 μm or more.

The rough section is provided on the cell culture substrate surface so that the distance between the adjacent rough sections is at least 10 μm or more. Here, the distance between the adjacent rough sections is a minimum value of distance from the edge of one of adjacent rough sections to the edge of the other rough section. The distance between the rough sections ranges from 10 μm to 4,045 μm, preferably from 10 μm to 3,220 μm, and more preferably from 10 μm to 1,200 μm. When the distance between the adjacent rough sections is within the range of values described above, the cancer cell aggregate can be formed. However, in terms of forming the cancer cell aggregate more efficiently, it is preferable to set the shortest distance between the rough sections provided on a single cell culture substrate to be shorter within the range described above, for example, from 10 μm to 120 μm, preferably from 10 μm to 80 μm, more preferably from 10 μm to 60 μm, and furthermore preferably from 10 μm to 40 μm.

As will be described below, the cancer cell aggregate in the second aspect is formed on the cell culture substrate in the first aspect so as to stretch across the rough sections, by the aggregation and self-organization of cancer cells. It is presumed that if the distance between the rough sections is shorter than the length of a single cell, cancer cells may grow on the rough sections, but cannot identify the rough sections as multiple rough sections. Thus, the formation of a cancer cell aggregate will not be induced. Consequently, the distance between the rough sections is suitably adjusted within the range described above according to the size of cells to be cultured so that the distance becomes longer than the length of a single cell to be cultured.

Moreover, due to the same reason, when the depth of the rough section is deeper than the length of a single cell to be cultured, it is presumed that the cancer cells cannot move out from the rough section, and thus a cancer cell aggregate will not be formed. Consequently, it is preferable to set the depth of the rough sections shallower than the length of a single cell to be cultured.

The rough section in the first aspect of the present invention has an uneven structure ranging from 20 nm to 200 nm in height on the rough section surface. The height of the uneven structure is the absolute value of the depth of a concave and the height of a convex from the reference surface of a single rough section surface. The height of the uneven structure on the rough section surface ranges from 20 nm to 200 nm, preferably from 30 nm to 100 nm, and more preferably from 40 nm to 60 nm. Here, the "reference surface" is the surface of a base material without a biocompatible polymer layer, in other words, the surface of a base material before the biocompatible polymer layer is formed.

It is preferable that the degree of unevenness on the rough section surface is such that the developed interfacial area ratio (Sdr) of the rough section surface is about 0.002 or more. Sdr is one of surface property parameters defined in International Standard ISO 25178. Sdr represents how much the developed surface (surface area) of a defined area is increased with respect to the area of the defined area, and Sdr of a completely flat surface will be zero. As for the rough section surface in the present invention, Sdr is an index indicating how much the surface area of a single rough section having an uneven structure is increased by the unevenness, compared with the area of the same shape that is presumed to be complete flat. In the present invention, Sdr of the rough section surface is 0.002 or more, preferably 0.003 or more, and more preferably 0.004 or more.

Moreover, in a specific embodiment, it is preferable that the arithmetic mean roughness (Ra) of the rough section surface be 4 nm or more, the maximum height roughness (Rz) be 30 nm or more, or the arithmetic mean peak curvature (Spc) be 300 or more. Ra and Rz are surface property parameters defined in Japan Industrial Standard (JIS) B 0601-2001 and ISO 13565-1, and Spc is a surface property parameter defined in ISO 25178.

Ra is a parameter representing the average of Z(x) absolute value in the reference length, when the contour curve is a roughness curve. As for the rough section surface in the present invention, Ra is an average of the absolute values of the depth of concave and the height of convex, from the reference surface of a single rough section surface. Ra of the rough section surface in the present invention is 4 nm or more, preferably 5 nm or more, and more preferably 6 nm or more.

Rz is a parameter representing a sum of the height (Zp) of the highest peak and the depth (Zv) of the deepest valley in the contour curve in the reference length, when the contour curve is a roughness curve. As for the rough section surface in the present invention, Rz is a sum of the absolute values of the depth of the deepest valley and the height of the highest peak from the reference surface of a single rough section surface. Rz of the rough section surface in the present invention is 30 nm or more, preferably 40 nm or more, and more preferably 50 nm or more.

Spc is a parameter representing the average of the principle curvature of the peak point of the surface, and when Spc is a small value, the peak point is rounded, and when Spc is a large value, the peak point is sharp. Spc of the rough section surface in the present invention is 300 or more, preferably 400 or more, and more preferably 600 or more.

In the first aspect, the number of rough sections provided on the cell substrate surface is not limited as long as the shape of the rough section and the distance between the rough sections are within the range described above. For example, the total area of the rough sections is suitably set so as to range from 0.03 to 65% of the surface area of the cell culture substrate. Moreover, similarly, a dispersion degree of the rough sections on the cell culture substrate surface is not limited, as long as the shape of the rough section and the distance between the rough sections are within the range described above. Furthermore, all of the numerical parameters described above such as the distance between the rough sections; the height of unevenness on the rough section surface; the contour shape and diameter of the spot; and the width, the length and the shape of the groove, and the like; may be the same among the rough sections on a single cell culture substrate, or some or all of the parameters may differ among the rough sections. Still furthermore, the rough sections may be disposed regularly or irregularly. For example, the shape of the rough section on a single cell base material surface may only be spots, grooves, or a mixture of spots and grooves. Still furthermore, for example, when the shape of the rough section is a groove, another groove may be provided in the extending direction of a single groove, and another groove may be provided at a position parallel to the single groove.

Figure 2:
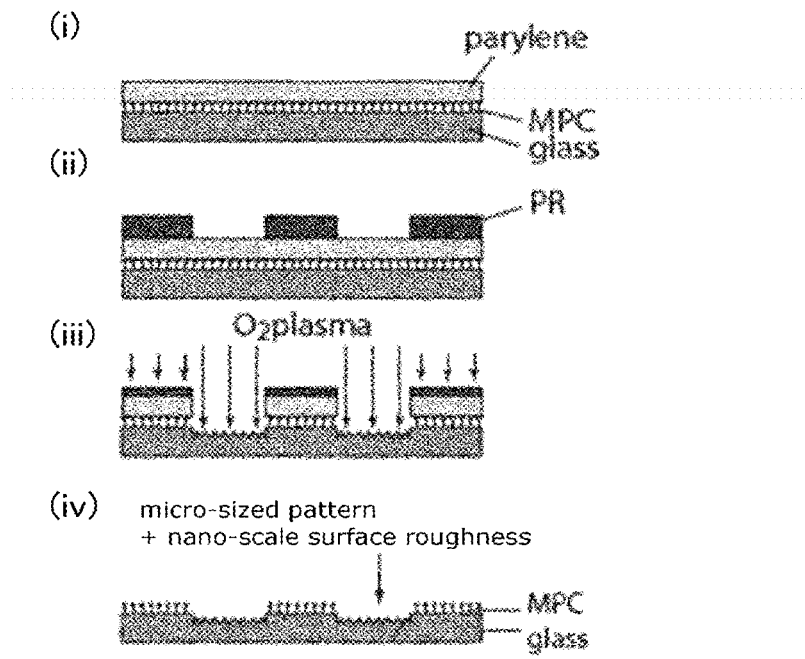
FIG. 2 includes diagrams illustrating a production procedure of a cell culture substrate.

By designing the shape of the rough section, the distance between the rough sections, and the uneven structure of the rough section surface to be as above, the cell culture substrate in the first aspect can be produced according to the patterning method of a biocompatible polymer disclosed in WO2010/032846 (Patent Literature 1, the entire disclosure of which is hereby incorporated in the present specification by reference). FIG. 2 is a typical schematic example of this method.

First, a biocompatible polymer (MPC polymer) layer is formed on a glass base material, and a resin (polyparaxylylene such as Parylene (registered trademark)) layer is then formed thereon (FIG. 2(i)).

For example, the biocompatible polymer layer and the resin layer may also be produced by thinly applying the polymers on the base material surface, or may be produced by attaching a thin layer made of the polymers to the base material surface. The biocompatible polymer layer and the resin layer may also be produced by coating a monomer serving as a constitutional unit of the polymers on the base material surface, and causing a polymerization reaction to take place. Moreover, in the typical example, the biocompatible polymer layer is formed so as to come into contact with the base material. However, a layer of another substance may also be provided between the base material and the biocompatible polymer layer.

Next, after forming an aluminum and photoresist layer on the resin layer (FIG. 2(ii)), oxygen ($O_2$) plasma is emitted from above the aluminum and photoresist layer. By adjusting the emission intensity and time of $O_2$ plasma, the resin layer and the biocompatible polymer layer of a portion that is not protected by the aluminum and photoresist layer are removed, and a portion where the glass base material is exposed is formed. At the same time, an uneven structure is formed on the surface (FIG. 2(iii)). Then, by removing the resist layer, the cell culture substrate in the first aspect the substrate surface of which has the rough sections not covered with the biocompatible polymer layer is obtained (FIG. 2(iv)).

In the typical example described above, $O_2$ plasma is used to form the portion where the base material is exposed by removing the resin layer and the biocompatible polymer layer. $O_2$ plasma is also used to form the uneven structure on the surface. However, a dry etching method, a wet etching method, and other methods known to a person skilled in the art may also be used.

The cell culture substrate in the first aspect is suitable for culturing adherent cells. The cells that have come into contact with the substrate cannot attach to a biocompatible polymer layer without non-specific adsorption properties to cells, and proliferate by attaching only to the rough section that is not covered with the biocompatible polymer layer and that has an uneven structure of nanometer order.

The present inventors have found out that when adherent cancer cells are cultured using the cell culture substrate in the first aspect, the cancer cells unexpectedly form a cancer cell aggregate formed in a shape stretching across the rough sections, which are used as an anchorage, by the aggregation and self-organization of the cancer cells during culture.

2. Cancer Cell Aggregate and Method for Producing the Same

A second aspect of the present invention relates to a cancer cell aggregate that has the following characteristics (a) to (e), that is formed of adherent cancer cells, and that is isolated and alive:
(a) having cell-in-cell structure,
(b) having non-spheroidal morphology,
(c) having membranous expression of α-tubulin on surface,
(d) having morphological polarity, and
(e) having tissue motion polarity.

The cancer cell aggregate in the second aspect may also have at least one of the following characteristics (f) to (k):

(f) having capability to reversibly release and incorporate live cancer cells,
(g) having cilia on surface,
(h) exhibiting filipodia or lamellipodia morphology,
(i) having capability to incorporate dead cells,
(j) having cell debris suction force, and
(k) having phosphatidylserine-positive surface.

Figure 3:
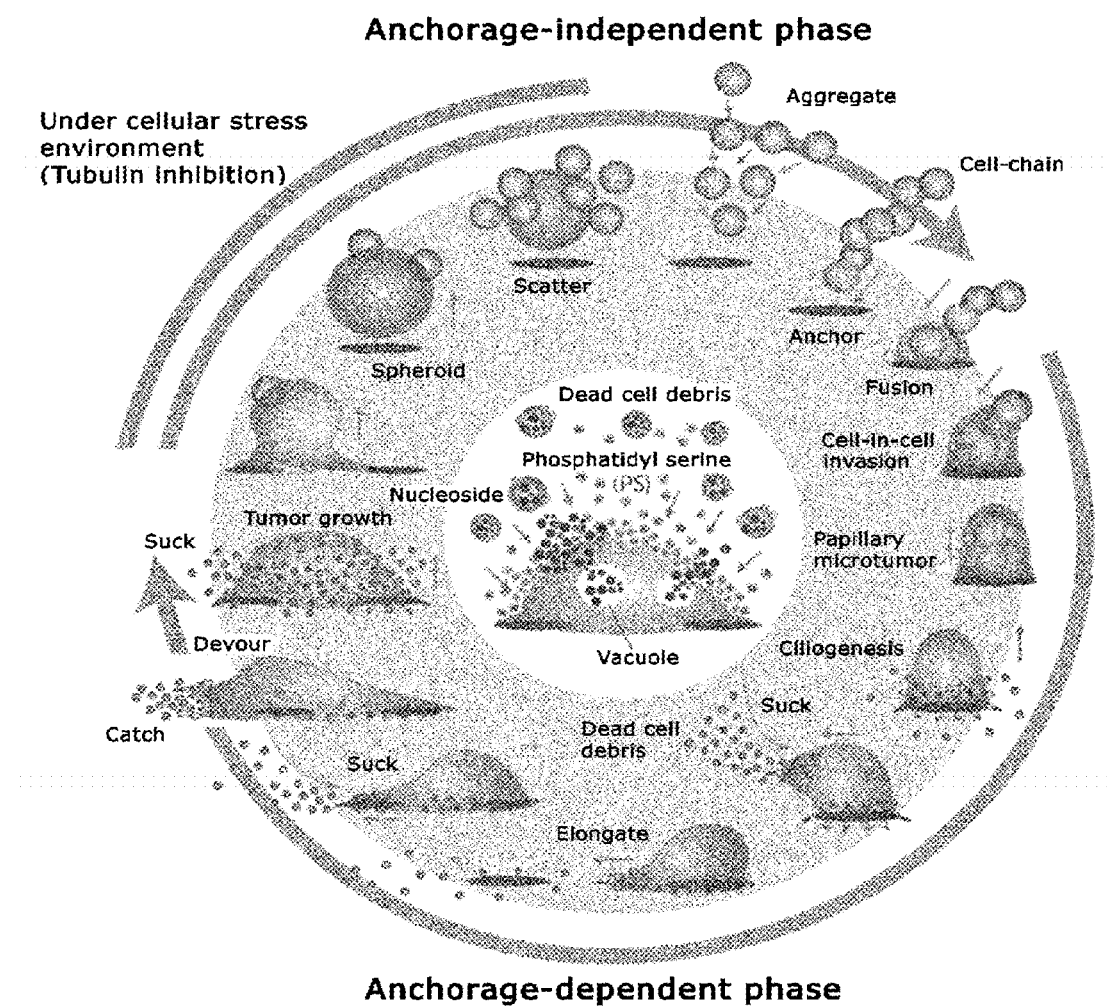
FIG. 3 is an image diagram of a life cycle of microtumor.

The cancer cell aggregate in the second aspect is a non-spheroidal cancer cell mass that has morphological polarity and tissue motion polarity, that is self-organized, and that is anchorage-dependent. It is presumed that the cancer cell aggregate in the second aspect has a life cycle as if it would be a single creature, as illustrated in FIG. 3. In FIG. 3, a cell aggregate in an anchorage-dependent phase corresponds to the cancer cell aggregate in the second aspect of the present invention. The cancer cell aggregate in the second aspect is isolated and alive. Here, "isolated" means that the cancer cell aggregate is not under in vivo environment, but under in vitro environment. Hereinafter, the characteristics of the cancer cell aggregate will be described in detail with reference to FIG. 3.

In cancer cells seeded in a culture medium, single cells aggregate with each other, and become a chained assembly in which the cells are chained together. Next, the chained assembly is attached to an attachable structure, which is to be an anchorage, typically, an uneven structure on the rough section surface of the cell culture substrate in the first aspect. The chained assembly anchored to the anchorage becomes a cancer cell aggregate (also referred to as a "microtumor") that has a cell-in-cell structure covered by membranous expression of α-tubulin (presumed to be a microtubule), by a phenomenon called entosis in which a cell is incorporated into another cell. This entosis is reversible, and the microtumor not only incorporates live cancer cells but also releases the cells as live cancer cells.

The microtumor grows into a papillary shape in the height direction, and ciliogenesis is induced on its lower layer surface. Moreover, with the growth, the microtumor will have morphological polarity and tissue motion polarity. Here, the morphological polarity is a tendency to be formed into a biased shape depending on the surrounding state, and the tissue motion polarity is a tendency to advance in a biased direction depending on the surrounding state. More particularly, the microtumor forms filipodia or lamellipodia, catches and engulfs the dead-cell debris present in the surroundings by using the filipodia or lamellipodia. In addition, the microtumor exhibits active motility, advances from the attached rough section to the adjacent rough section so as to seek the dead-cell debris, and is formed into a shape so as to stretch across the rough sections. The microtumor also has a powerful suction force to catch the surrounding debris. By using the filipodia, the lamellipodia, and the suction force, the microtumor that has actively engulfed the dead-cell debris further grow into a massive shape.

Nucleoside derived from dead-cell debris that is engulfed by a microtumor, is incorporated into vacuoles of the microtumor, while phosphatidylserine derived from dead cell debris is accumulated on the surface of the microtumor. The microtumor not only exhibits phosphatidylserine once incorporated therein on the surface, particularly on the external surface thereof by turnover, but also accumulates phosphatidylserine on the external surface by attracting the dead-cell debris therearound, by the powerful suction force. In this manner, one of the characteristics of the microtumor is the presence of phosphatidylserine on the surface, in particular, the presence of phosphatidylserine on the external surface, in other words, externalization. That is, the microtumor displays a dead-cell phenotype. Thus, it is considered that this phenotype contributes to an escape of microtumors from an attack by immune system cells, in other words, cancer immune evasion.

The microtumor moves away from the anchorage under cellular stress environment such as the presence of a microtubule polymerization inhibitor and the like, to have spheroidal morphology. In addition to the morphological change, the characteristics of microtumors such as the cell-in-cell structure, the membranous expression of α-tubulin, the morphological polarity, the tissue motion polarity, and the phosphatidylserine-positive aggregate surface will also be lost. Due to loss of the cell-in-cell structure, the cancer cells that have formed the microtumor are released from the aggregate as single cancer cells, and are scattered on the surroundings. When the cellular stress environment is removed, the cancer cells form a new anchorage-dependent microtumor again.

In this manner, the cancer cell aggregate in the second aspect of the present invention greatly differs from a spheroidal cell mass conventionally observed in the three-dimensional culture of cancer cells. The cancer cell aggregate in the second aspect can be utilized as an evaluation system for the collective cell migration of cancer cells. The system is expected as an evaluation system representing a series of cancer progression such as development, proliferation, infiltration, metastasis, and recurrence of cancer in vivo. Actually, a structure that has the same characteristics as those of the cancer cell aggregate in the second aspect has been observed in laboratory animals implanted with cancer cells, and pathological specimens of cancer patients. For example, as will be described in the following examples, the present inventors have confirmed that a cancer cell aggregate formed from pancreatic ductal adenocarcinoma has a similar structure to that of the luminal structure identified in the specimens of pancreatic ductal adenocarcinoma patients.

The cancer cell aggregate in the second aspect of the present invention is anchorage-dependent. Thus, the characteristics are lost when the cancer cell aggregate is placed in an environment without an anchorage, for example, on a conventional two-dimensional cell culture substrate. Hence, to maintain the cancer cell aggregate in the second aspect in vitro while keeping the characteristics, the cancer cell aggregate needs to be attached to a substrate having a structure to be an anchorage. Consequently, a third aspect of the present invention provides a complex consisting of a cell culture substrate having a three-dimensional structure and the cancer cell aggregate in the second aspect attached to the substrate. The cell culture substrate having a three-dimensional structure is not limited as long as the cell culture substrate provides an anchorage structure to which the cancer cell aggregate can be attached. A commercially available cell culture substrate for three-dimensional culture may be used, but preferably, the cell culture substrate in the first aspect will be used.

The cancer cell aggregate in the second aspect and the complex in the third aspect of the present invention can be produced by culturing adherent cancer cells using the cell culture substrate in the first aspect. Consequently, the present invention also provides a method for producing the cancer cell aggregate in the second aspect or the complex in the third aspect, including a step of culturing adherent cancer cells using the cell culture substrate in the first aspect.

Moreover, the complex in the third aspect of the present invention may also be produced by subculturing the cancer cell aggregate in the second aspect formed on the cell culture substrate in the first aspect, to another cell culture substrate having a three-dimensional structure.

The adherent cancer cells used for producing a cancer cell aggregate are preferably epithelial cancer cells. For example, the adherent cancer cells are cervical cancer cells such as HeLa cells, pancreatic cancer cells, lung cancer cells, colon cancer cells, or head and neck cancer cells; preferably pancreatic cancer cells, lung cancer cells, colon cancer cells, or head and neck cancer cells; and more preferably pancreatic ductal adenocarcinoma cells.

Cancer cells are cultured in a state that can come into contact with the cell culture substrate in the first aspect, typically, in a cell culture vessel mounted with the cell culture substrate. The culture conditions such as culture medium, culture temperature, and culture time other than the cell culture substrate are not limited as long as the conditions are normally used for culturing the cancer cells to be used. Coating of an extracellular matrix (ECM) is not necessary. For example, when pancreatic cancer cells, lung cancer cells, colon cancer cells, or head and neck cancer cells are used, a cancer cell aggregate in the second aspect that is made from these cells can be obtained, by culturing the cells in DMEM added with fetal bovine serum, at 37 degrees Celsius, for about overnight to 48 hours. Because the time required for forming the cancer cell aggregate differs depending on the type of cancer cells, the culture time is suitably set according to the cancer cells to be used. Moreover, the morphology of cancer cell aggregate may differ depending on the cancer cells to be used. However, as long as the cancer cell aggregate has the characteristics (a) to (e) described above, the cancer cell aggregate is included in the second aspect of the present invention.

A known method normally used in cell biology and molecular biology can be used to confirm whether the obtained cancer cell aggregate has the characteristics described above. Methods for culturing cancer cells and for confirming the above characteristics are disclosed in standard textbooks and documents of the technical field such as "Molecular Cloning: A Laboratory Manual" (Sambrook & Russell, Cold Spring Harbor Laboratory Press, third edition, 2001), and "Animal Cell Culture: A Practical Approach" (edited by Masters, Oxford University Press, third edition, 2000). A person skilled in the art can culture cancer cells and confirm the above characteristics according to these descriptions or suitably altering the described methods. The entire contents of these literatures are hereby incorporated in the present specification by reference.

The cancer cell aggregate in the second aspect and the complex in the third aspect of the present invention are considered to reproduce in vitro a series of flow in vivo of development, proliferation, infiltration, metastasis, and recurrence of cancer. Consequently, the cancer cell aggregate and the complex can be utilized as research tools for cancer research, in particular, for researching collective cell migration of cancer cells. In particular, pancreatic ductal adenocarcinoma, which accounts for about 90% of pancreatic cancers, is one type of the lethal malignant tumors, and is aggressive cancer that progresses rapidly by frequent DNA damage and mitotic abnormalities. However, dynamics of live pancreatic ductal adenocarcinomas is not yet elucidated. Consequently, the cancer cell aggregate and the complex produced using pancreatic ductal adenocarcinoma cells are useful in screening for new drugs which contribute to prevention and/or treatment of pancreatic ductal adenocarcinoma. Moreover, in the cancer cell aggregate in the second aspect, the induction of ciliogenesis, the enhancement of endocytosis, and the coating of external surface by phosphatidylserine are identified. Because phosphatidylserine has a strong immunosuppression effect, it is considered that cancer immune evasion is induced in the cancer cell aggregate in the second aspect. The cancer immune evasion is an unsolved major problem in cancer treatment. Thus, the cancer cell aggregate in the second aspect and the complex in the third aspect can be utilized as research tools in cancer immunity research. Furthermore, because high expression of microtubule-associated protein light chain 3 (LC3), which is the key protein in autophagy, is confirmed, it is considered that autophagy is enhanced. Consequently, the cancer cell aggregate in the second aspect and the complex in the third aspect can also be utilized as research tools for autophagy research in the cancer tissue level.

3. Screening Method

A further aspect of the present invention relates to a method for screening a drug for preventing and/or treating cancer, including a step of making the cancer cell aggregate in the second aspect coexist with a test substance; a step of observing the above cancer cell aggregate for at least one of the following characteristics:

(a) having cell-in-cell structure,
(b) having non-spheroidal morphology,
(c) having membranous expression of $\alpha$-tubulin on surface,
(d) having morphological polarity,
(e) having tissue motion polarity,
(f) having capability to reversibly release and incorporate live cancer cells,
(g) having cilia on surface,
(h) exhibiting filipodia or lamellipodia morphology,
(i) having capability to incorporate dead cells,
(j) having cell debris suction force, and
(k) having phosphatidylserine-positive surface, and making a comparison with those of the cancer cell aggregate in the second aspect that is not made to coexist with the test substance; and a step of determining that the test substance has an anticancer activity when attenuation or loss of the above characteristics is more strongly observed in the coexistence with the test substance.

Another further aspect of the present invention relates to a method for screening a drug for preventing and/or treating cancer, including a step of making the cancer cell aggregate in the second aspect coexist with a test substance; a step of measuring the length or size of the above cancer cell aggregate or pseudopodium thereof and making a comparison with that of the cancer cell aggregate in the second aspect that is not made to coexist with the test substance; and a step of determining that the test substance has an anticancer activity when the cancer cell aggregate or the pseudopodium becomes shorter or smaller in the coexistence with the test substance.

The cancer cell aggregate in the second aspect of the present invention reproduces in vitro a series of flow in vivo of development, proliferation, infiltration, metastasis, and recurrence of cancer, and the substance that attenuates or removes the characteristics of the aggregate is considered to serve as a drug for particularly inhibiting infiltration and metastasis of cancer, in other words, a drug for preventing and/or treating metastasis and/or recurrence of cancer. Consequently, by comparing the characteristics described above of the cancer cell aggregate made to coexist with a test substance with those of the cancer cell aggregate in the absence of the test substance, it is possible to perform screening for a drug for preventing and/or treating cancer.

Moreover, particularly when a cancer cell aggregate is formed by using the cell culture substrate in the first aspect in which the shape of the rough section is a groove, the cancer cell aggregate develops many pseudopodia along the extending direction of the groove. It is considered that a substance that reduces the length or size of the cancer cell aggregate itself or the pseudopodia may become a drug for particularly inhibiting infiltration and metastasis of cancer, in other words, a drug for preventing and/or treating metastasis and/or recurrence of cancer. Consequently, by comparing the length or size of the cancer cell aggregate made to coexist with a test substance or the pseudopodia with those of a cancer cell aggregate in the absence of the test substance, it is possible to perform screening for a drug for preventing and/or treating cancer.

A cancer cell aggregate and a test substance may be made to coexist by adding the test substance to a culture medium used for culturing a cancer cell aggregate or a suitable buffer solution. The culture medium or the buffer solution is brought into contact with a cancer cell aggregate attached to the cell culture substrate having a three-dimensional structure, and the presence or a degree of at least one of the characteristics described above, or the length or size of the cancer cell aggregate or the pseudopodia are compared with those of the cancer cell aggregate for comparison that is brought into contact with a culture medium or a buffer solution not containing the test substance. When the evaluation parameter described above is attenuated or lost in the presence of the test substance, the test substance is a substance that works for the cancer cell aggregate in an inhibitory manner, and is selected as a candidate drug for preventing and/or treating cancer.

As described above, the cancer cell aggregate in the second aspect has immune evasion capability to evade attacks from the immune system. Consequently, the screening method according to the present aspect is particularly useful in screening for a drug for inhibiting and/or releasing the immune evasion mechanism in cancer.

4. Method for Determining Anoikis Resistance in Epithelial Cancer Cells

Another still further aspect of the present invention relates to a method for determining anoikis resistance in epithelial cancer cells including a step of culturing test epithelial cancer cells using the cell culture substrate in the first aspect; and a step of determining that the epithetical cancer cells have anoikis resistance when the epithetical cancer cells have proliferated without adhering to the cell culture substrate.

Unlike the conventional cell culture substrate, the cell culture substrate in the first aspect of the present invention has properties that, when epithetical cancer cells without anoikis resistance are cultured, the cells adhere and proliferate to form a cancer cell aggregate; and that, when epithetical cancer cells with anoikis resistance are cultured, the cells proliferate without adhesion. Consequently, when test epithelial cancer cells are cultured using the cell culture substrate in the first aspect, and when the cells proliferate without adhering to the substrate, it is possible to determine that the cells have anoikis resistance, in other words, have a mesenchymal phenotype. Moreover, the acquisition of anoikis resistance is a phenomenon correlating with EMT experience and infiltrative and metastatic capacity. Thus, the present aspect may also be referred to as a method for determining EMT experience in epithelial cancer cells, and a method for evaluating the infiltrative and metastatic capacity of the epithelial cancer cells.

The present invention will be described further in detail with the following examples. However, the present invention is not limited to these examples.

EXAMPLES

Materials
1) Cells and Culture Medium
Human pancreatic ductal adenocarcinoma cell lines: PCI-55, PCI-24, and PCI-43 (all cell lines were established from primary lesion tissues of pancreatic cancer surgically resected at Hokkaido University Hospital, and have heterozygous KRAS G12D mutation (KRASG12D/WT)), PANC-1 (ATCC), and MIA PaCa-2 (JCRB cell bank)
Human lingual cancer cell lines: HSC-3 (JCRB cell bank) and SCC-9 (ATCC)
Human lung cancer cell lines: H1975 (ATCC) and A549 (JCRB cell bank),
Human colon cancer cell lines: DLD-1 and WiDr (both from JCRB cell bank)
the cancer cell lines described above were subcultured in DMEM containing 10% fetal bovine serum (FBS), and penicillin/streptomycin.
Normal human embryonic pancreas derived cell line: 1C3IKEI (Riken BioResource Center) maintained in DMEM containing 15% FBS.
Human NK cell line: KHYG-1 (JCRB cell bank) subcultured in RPMI-1640 culture medium containing 100 U recombinant human IL-2, 10% FBS, and penicillin/streptomycin.

2) Reagents
DAPI (Vector Laboratories Inc.) or Hoechst 33342 (Molecular Probes) was used for staining cell nucleus. Alexa Fluor (registered trademark) 488-labeled phalloidin (Phalloidin, Molecular Probes) was used for staining actin. Mouse anti-human α-tubulin monoclonal antibody (clone DM1A, eBioscience) was used for immunostaining α-tubulin. Rabbit anti-LC3B/MAPLC3B polyclonal antibody (Novus Biologicals) was used for immunostaining microtubule-associated protein light chain 3B (LC3B). Alexa Fluor-labeled anti-human IgG Goat polyclonal antibody (Molecular Probes) was used as a secondary antibody for immunofluorescence staining. ENVISION kit/HRP (DAB)(DAKO) was used for the color development of immunohistochemical staining. 5- (and 6-)carboxyfluorescein diacetate succinimidyl ester (CFSE, Dojindo Laboratories) and PKH26 (Sigma-Aldrich) were used for staining live cells. Annexin V Alexa Flour 488 (Molecular Probes) was used for staining phosphatidylserine. Ethidium homodimer (EthD-1; Molecular Probes) was used for nuclear staining dead cells.

Moreover, Tissue-Tek O.C.T. Compound (Sakura FineTek Japan) was used for producing frozen tissue slices of mouse peritoneum. LSAB2 Kit/HRP (DAKO) was used for detecting immunostained formalin-fixed pancreatic duct tissue slices from a pancreatic ductal adenocarcinoma patient. FluoSpheres carboxylate-modified microspheres (0.2 µm yellow-green fluorescence; Molecular Probes) was used for tracking the flow of culture medium. Cell Navigator (trademark) Lysosome Staining Kit Red Fluorescence (AAT Bioquest) was used for live imaging of lysosome. Click-iT (registered trademark) Plus EdU Alexa Fluor (registered trademark) 594 Imaging Kit (Molecular Probes) was used for detecting 5-ethynyl-2'-deoxyuridine (EdU) which is a nucleoside analog. Nocodazole (Sigma-Aldrich) was used as a microtubule inhibitor.

3) Statistical Analysis
By using Student's t-test and repeated measures analysis of variance, P value of 0.05 or less was considered a significant difference.

Example 1

Production of Cell Culture Substrate and Measurement of Surface Roughness Parameter An MPC polymer layer with 40 nm in average thickness (when wet) was formed by spin coating MPC polymer liquid on a glass base material (20 mm×20 mm). Then, a polyparaxylene (Parylene (registered trademark)) layer with 1 μm in thickness was vapor-deposited on the MPC polymer layer. An aluminum and photoresist layer was also formed thereon.

Figure 4:
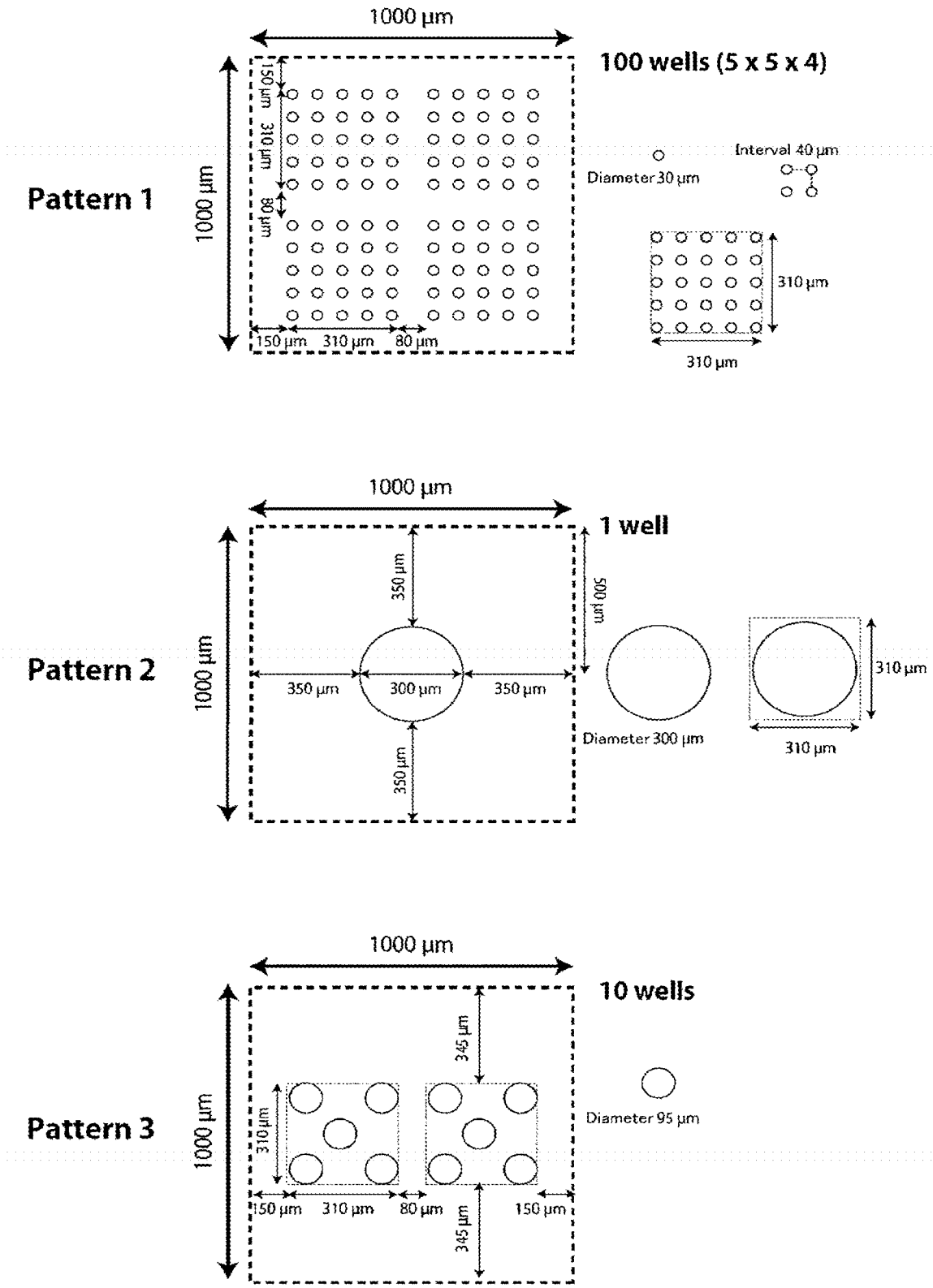
FIG. 4 includes diagrams illustrating micro-patterns of a cell culture substrate. Spots in Pattern 1 are 30 μm in diameter, a spot in Pattern 2 is 300 μm in diameter, and spots in Pattern 3 are 95 μm in diameter.
Figure 5:
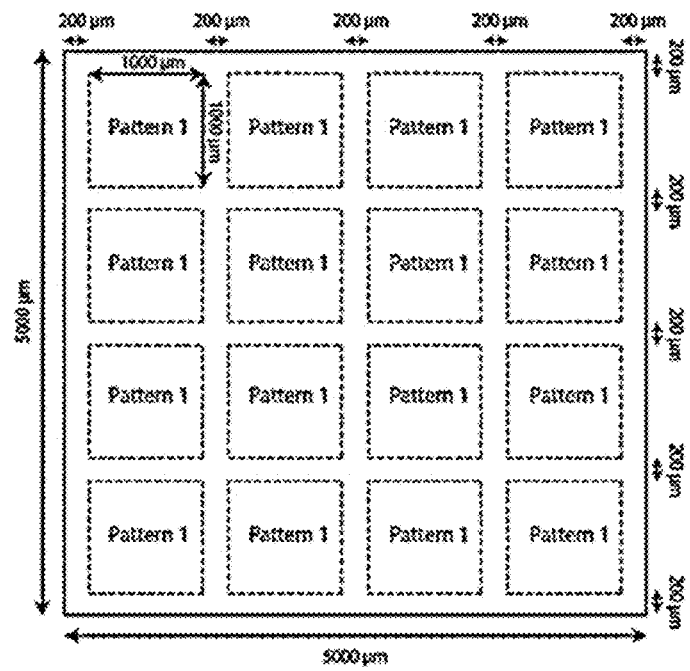
FIG. 5 includes diagrams illustrating the entire structure of the cell culture substrate of Pattern 1.
Figure 5:
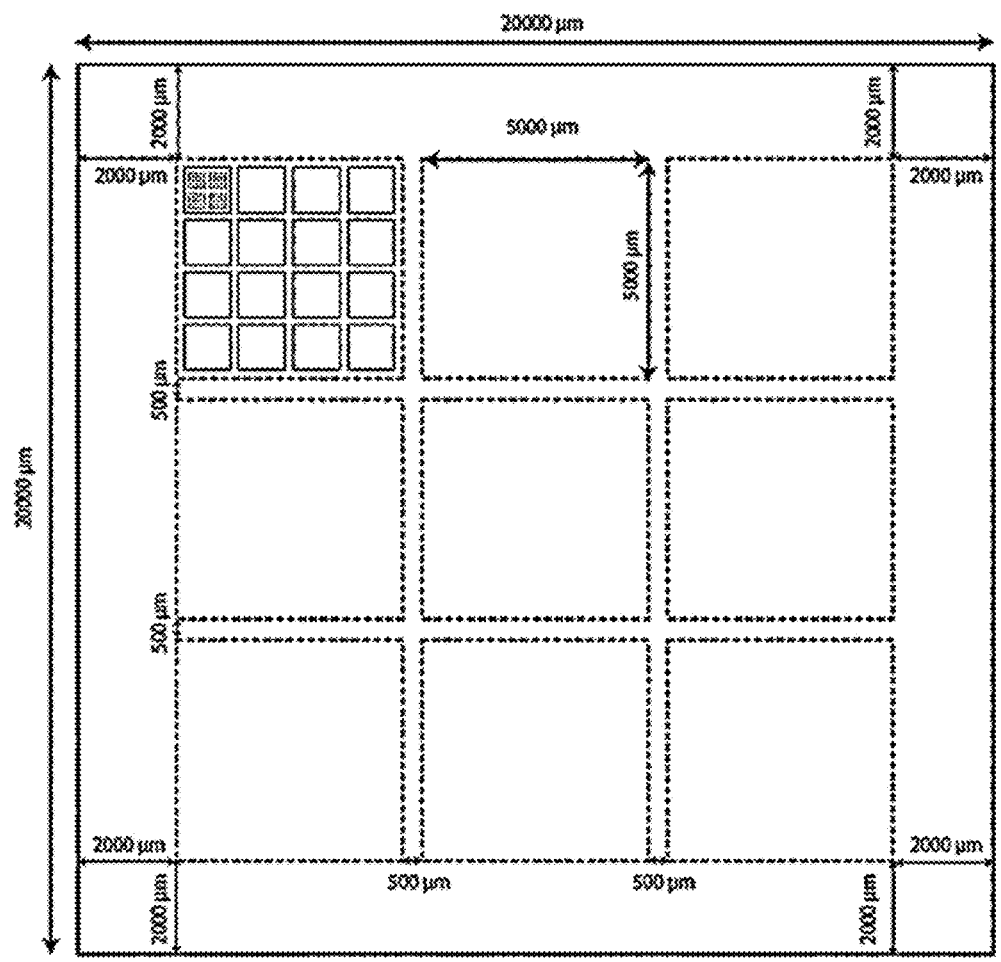

An electron beam drawing device (ELS-3700, ELIONX), an EB heating/resistant heating-type vacuum evaporation apparatus (EBX-8C, Ulvac), a double-sided mask aligner (MA-6, Suss MicroTec), and a reactive ion etching device (RIE-10NR, SAMCO) were used to produce photomasks in which patterns having 100 pieces of circular spots of 30 μm in diameter per 1 mm$^2$ at 40 μm in the shortest interval (Pattern 1 in FIG. 4) are arranged as in FIG. 5, using a photolithography method. Then, the mask patterns were transferred to the photoresist layer.

Next, by emitting $O_2$ plasma using an inductively coupled plasma system (EIS-700, ELIONX), the polyparaxylene layer and the MPC polymer layer of an unmasked part were removed. Thus, patterned spots having an uneven structure were formed on the surface. The emission conditions of $O_2$ plasma were stage: 50 W, antenna: 300 W, and emission time: 4 minutes and 30 seconds.

After the plasma emission, a cell culture substrate with Roughness (+) was produced by detaching the remaining polyparaxylene layer. In this cell culture substrate, spots having an uneven structure on their surface are disposed as in Pattern 1 in FIG. 4, and a portion other than the spots is covered with the MPC polymer layer.

Moreover, a cell culture substrate with Roughness (−) for comparison without an uneven structure on the spot surface was produced by carrying out the work under the same conditions as described above including the patterning, except that the emission time of the $O_2$ plasma was set to 3 minutes and 30 seconds.

Figure 6:
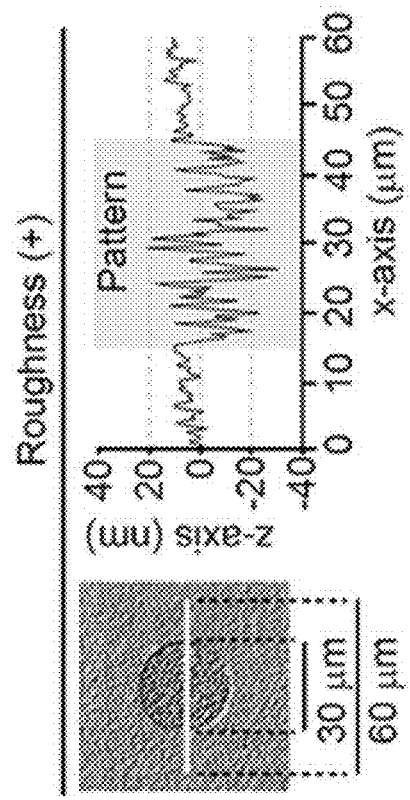
FIG. 6 includes photographs illustrating spot surfaces of cell culture substrates and diagrams illustrating unevenness in the height direction of the spot surfaces of the cell culture substrates. The left side represents a cell culture substrate with Roughness (−) for comparison having a flat spot surface, and the right side represents a cell culture substrate with Roughness (+) according to the present invention having an uneven structure on the spot surface.
Figure 6:
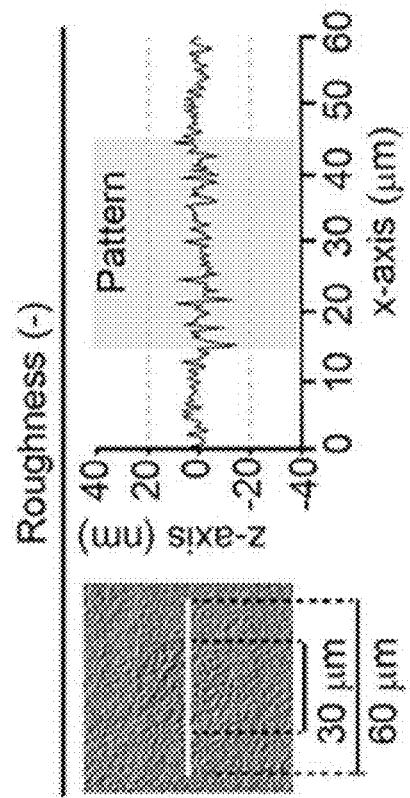

The roughnesses of the spot surfaces formed on the two types of cell culture substrates described above were measured by using a shape analysis laser microscope (VK-X250, KEYENCE). FIG. 6 is a graph illustrating the height of the spot surface using an xz coordinate system. While the spot surface of the cell culture substrate with Roughness (−) was substantially flat, it was confirmed that the spot surface of the cell culture substrate with Roughness (+) has an uneven structure of about 20 to 50 nm.

Figure 7:
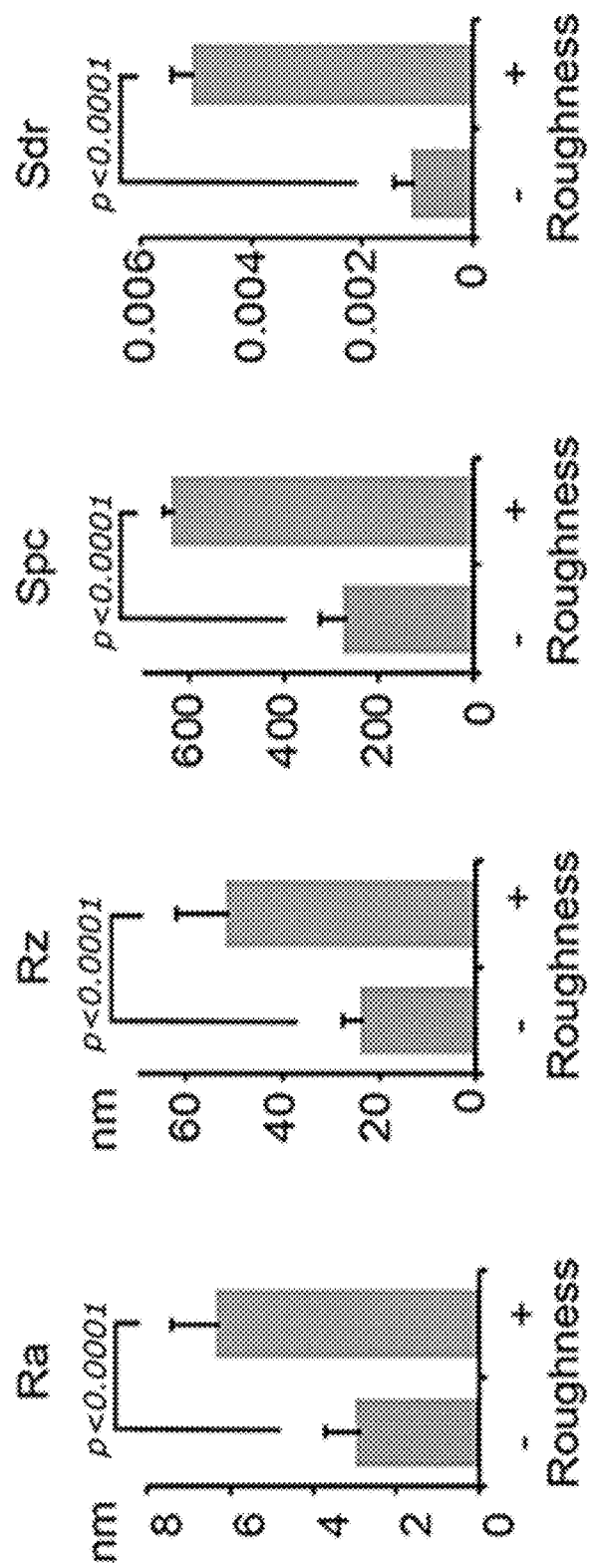
FIG. 7 includes graphs illustrating arithmetic mean roughness (Ra), maximum height roughness (Rz), arithmetic mean peak curvature (Spc), and developed interfacial area ratio (Sdr) of the spot surface of the cell culture substrate.

Moreover, FIG. 7 illustrates arithmetic mean roughness (Ra), maximum height roughness (Rz), arithmetic mean peak curvature (Spc), and developed interfacial area ratio (Sdr) of the spot surface of each of the cell culture substrates. Comparing to those of the spot surface of the cell culture substrate with Roughness (−), the parameters of the spot surface of the cell culture substrate with Roughness (+) all indicate high values. Particularly, the value of Sdr in the cell culture substrate with Roughness (+) was higher than that of the cell culture substrate with Roughness (−) by four times or more.

Example 2

Formation of Microtumors on Cell Culture Substrate with Spots Having Uneven Structure on Surface Cell culture substrates with Roughness (+) and (−) having a pattern in which a single circular spot of 300 μm in diameter is arranged per 1 mm$^2$ at 900 μm in interval (Pattern 2 in FIG. 4), and a pattern in which 10 pieces of circular spots of 95 μm in diameter are arranged per 1 mm$^2$ at about 57 μm in the shortest interval (Pattern 3 in FIG. 4) were produced as in Example 1. In Patterns 1 to 3 in FIG. 4, the proportion of the spot total area occupying the surface area of the cell culture substrate is about 7.1% in all cases.

A total of six types of cell culture substrates with Roughness (+) or Roughness (−) of 30, 95, or 300 μm in spot diameter were used to culture human pancreatic ductal adenocarcinoma cell line PCI-55. Immediately before culturing the cells, each of the cell culture substrates was immersed in distilled water for about 30 minutes to detach the polyparaxylene layer. Then, the cell culture substrate was washed using water, sterilized with 70% ethanol, and air dried. The cell culture substrate was then fixed to the inner bottom of a culture dish (Asnol petri dish, AS ONE) with 40 mm in diameter and 13.5 mm in depth via Vaseline. After adding DMEM and washing the cell culture substrate for three times, 3×10$^6$ of PCI-55 cells suspended in 3 mL of DMEM were seeded on each cell culture substrate, and cultured at 37 degrees Celsius overnight to for 48 hours.

Figure 8:
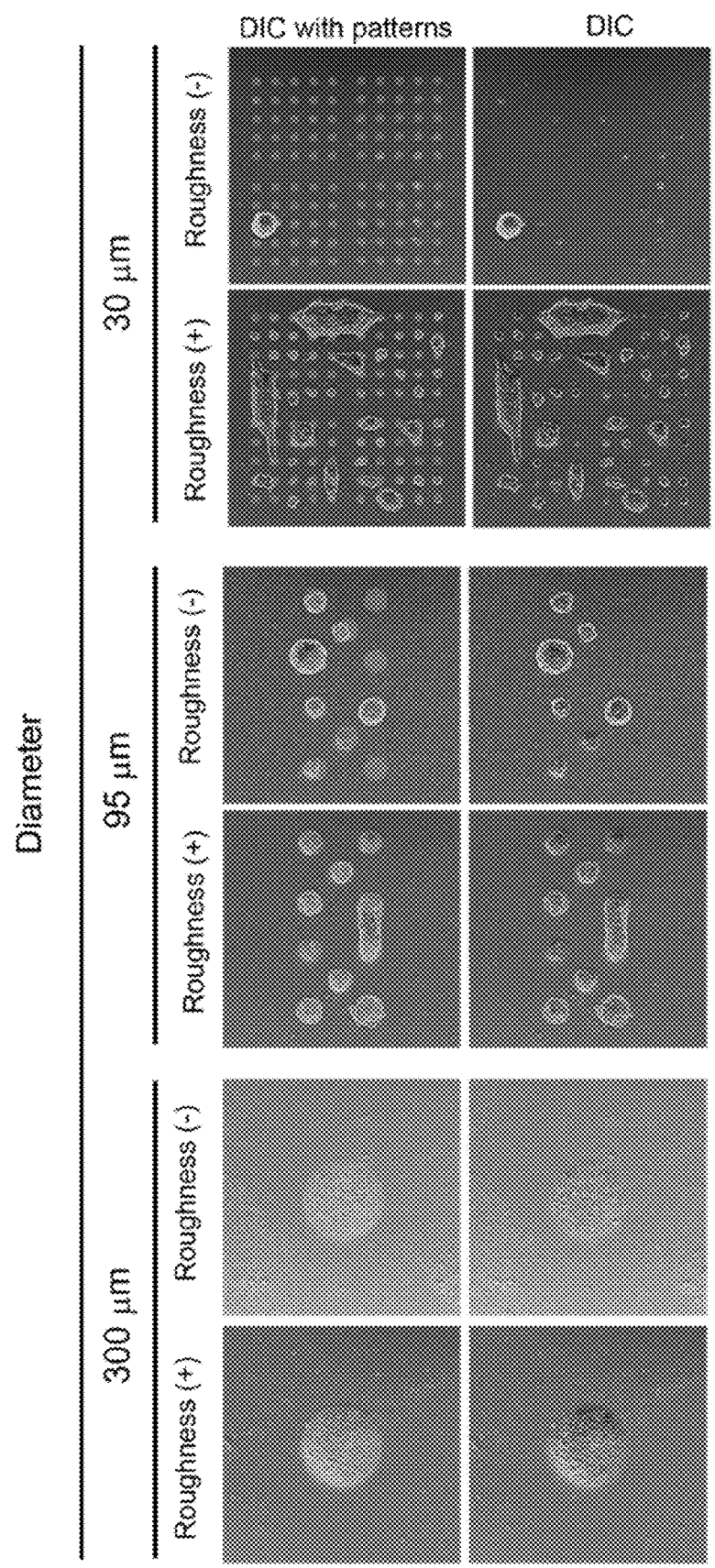
FIG. 8 includes observation images of KRAS-mutated human pancreatic ductal adenocarcinoma cell line PCI-55 cultured on cell culture substrates with spots 30 μm, 95 μm, and 300 μm in diameter respectively, using a differential interference microscope (DIC).

FIG. 8 includes observation images of the cell mass after being cultured, using a differential interference microscope (DIC). In the cell culture substrate with Roughness (−) of 30 μm in spot diameter, one or two cells adhered in the form of a monolayer on a single spot, and a spheroidal cell mass with a weak anchorage was sparsely formed. In the cell culture substrate with Roughness (−) of 95 μm in spot diameter, most of the cells adhered in the form of a monolayer on a spot, and a cell mass stretching across the spots was hardly observed. Moreover, the cells cultured using the cell culture substrate with 300 μm in spot diameter had the same morphology as that of the monolayer culture, regardless of the presence of Roughness on the substrate. In contrast, in the cell culture substrate with Roughness (+) of 30 μm or 95 μm in spot diameter, a plurality of papillary cell masses extending in the height direction were formed on a single spot, and a plurality of non-spheroidal cell masses strongly adhered to the spots stretching across two or more spots were formed.

Figure 9:
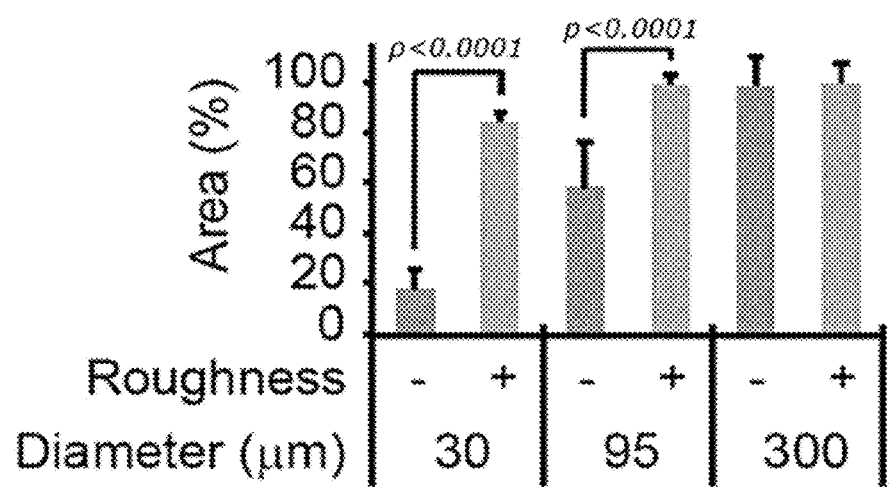
FIG. 9 is a graph illustrating the percentage of occupancy by cells (the number of spots to which cells adhere/the number of all spots) on the spot surface of the cell culture substrate.

NIS-Elements AR Ver 4.60.00 software (Nikon) was used to analyze the cell masses on the six types of cell culture substrates described above. FIG. 9 illustrates the percentage of occupancy by cells indicating percentages of the spots on the cell culture substrates being covered with cells. In the cell culture substrates with 30 μm and 95 μm in spot diameter, it was confirmed that the uneven structure on the spot surface has improved the percentage of occupancy by cells.

Figure 10:
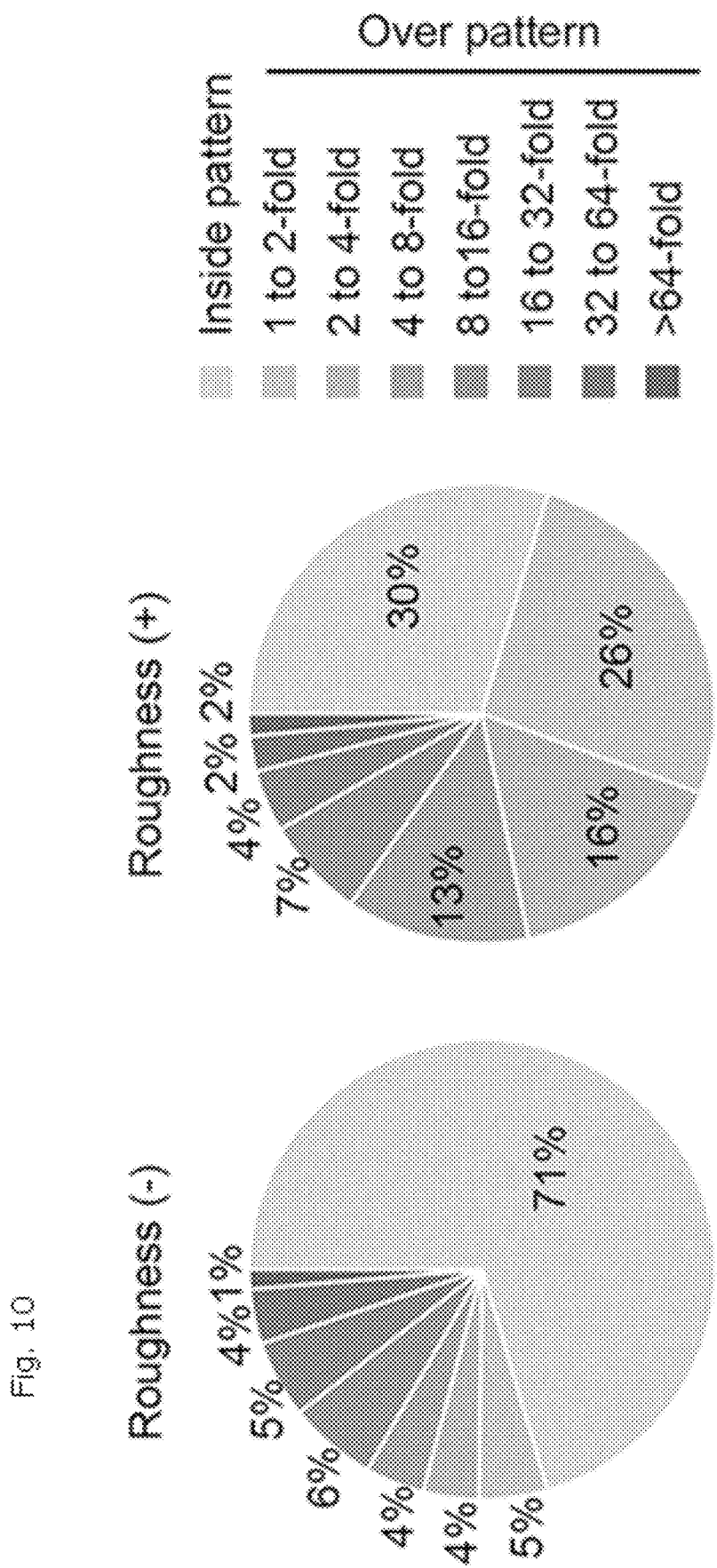
FIG. 10 includes pie charts in which the ratios between the bottom area of PCI-55 cell mass cultured on the cell culture substrate with spots 30 μm in diameter, and the surface area of a single spot are tabulated.

FIG. 10 illustrates pie charts in which the ratios between the bottom area of the cell mass formed by PCI-55 cells cultured on the cell culture substrate with Roughness (+) or (−) of 30 μm in spot diameter, and the surface area of a single spot are tabulated. When the ratio of the cell mass is greater than one fold, the cell mass has a shape protruding from a single spot. The uneven structure of the spot surface made the cell mass massive, and increased the proportion of the cell mass that has stretched across the spots.

Figure 11:
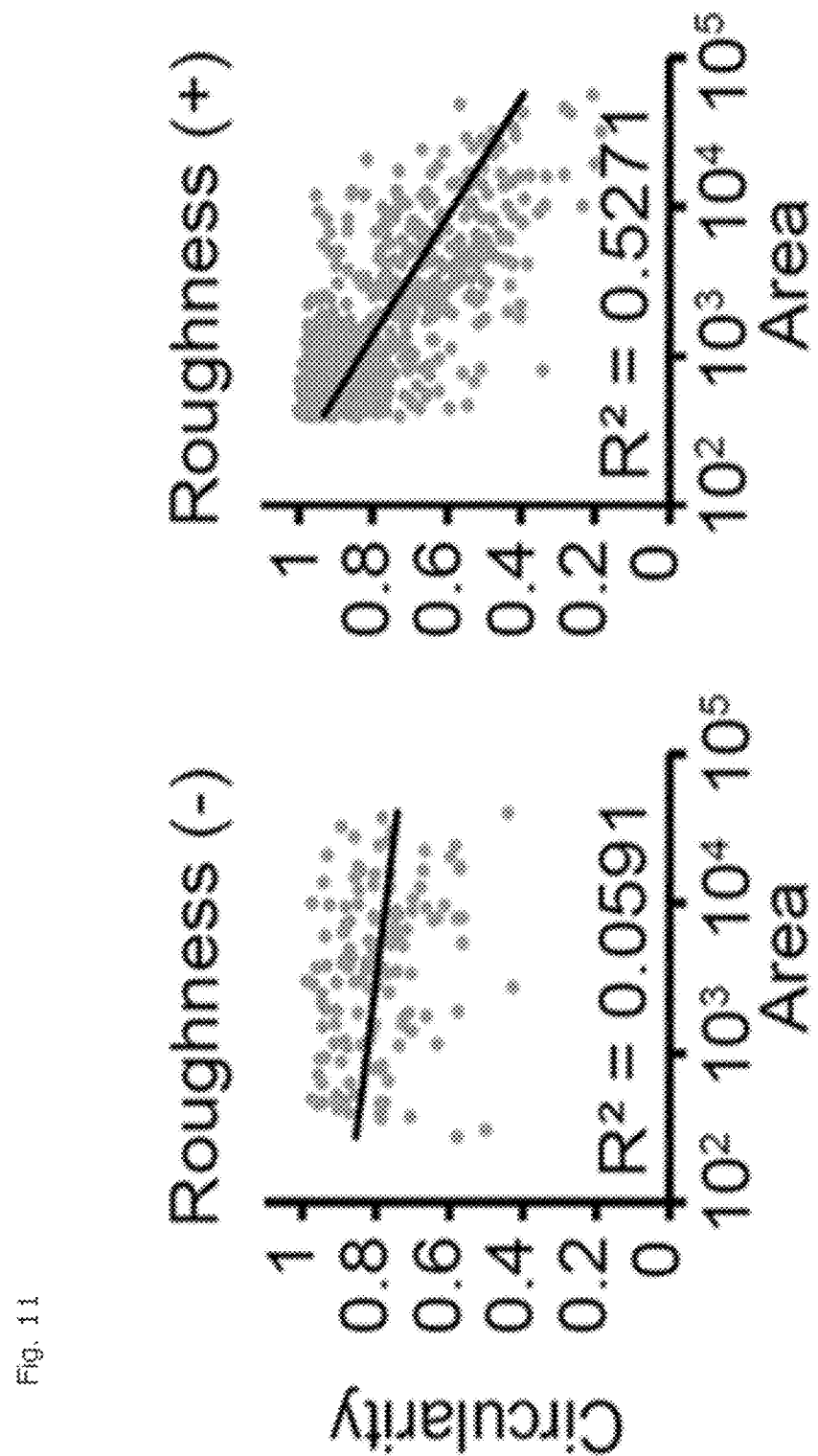
FIG. 11 includes scattered diagrams illustrating a correlation between the bottom area and the circularity of PCI-55 cell mass cultured on the cell culture substrate with spots 30 μm in diameter.

FIG. 11 illustrates a correlation between the bottom area and the circularity of the cell mass. In the cell culture substrate with Roughness (+), the circularity tended to decrease, in other words, the morphological polarity tended to increase with an increase in the bottom area. On the other hand, in the cell culture substrate with Roughness (−), such tendency was not identified.

Figure 12:
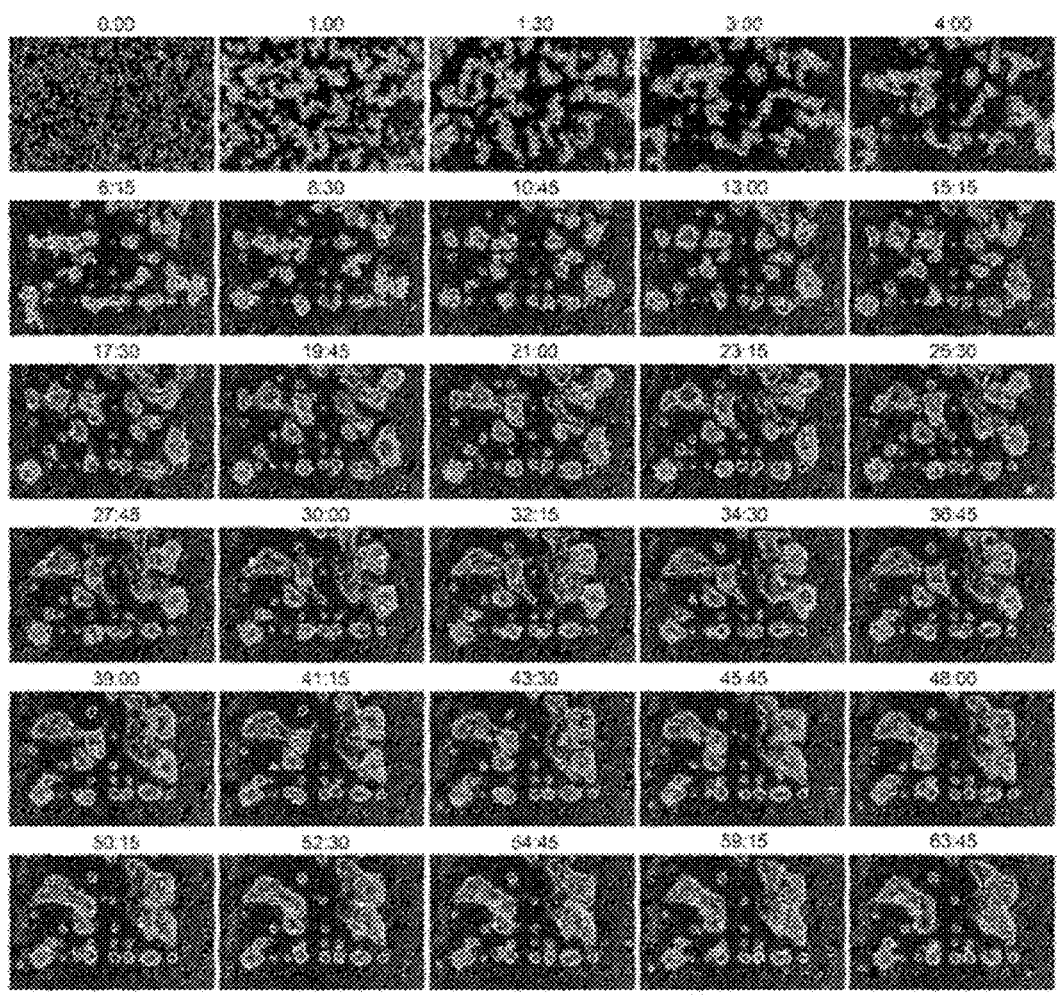
FIG. 12 includes time-lapse DIC images indicating states of PCI-55 cells seeded on a cell culture substrate with Roughness (+) of 30 μm in spot diameter (hereinafter, referred to as a "cell culture substrate 1") forming microtumors.
Figure 13:
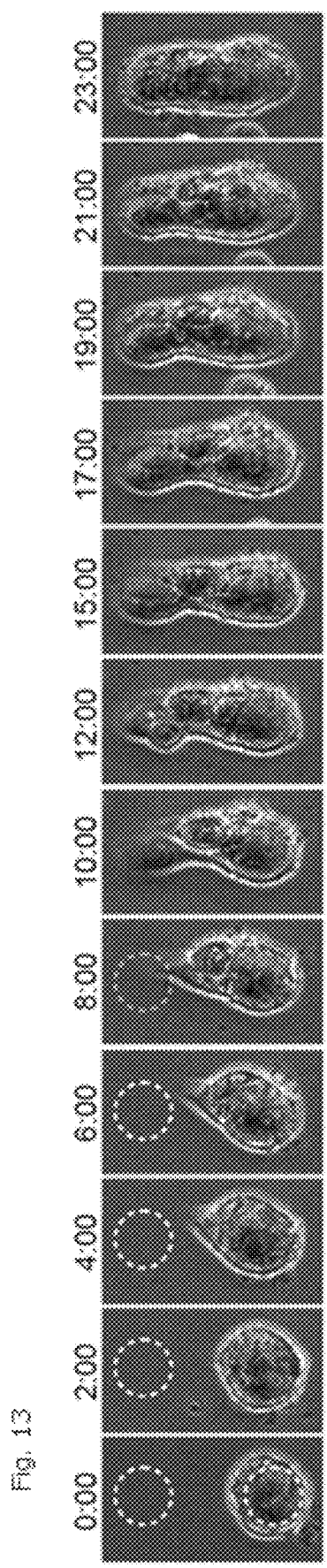
FIG. 13 includes time-lapse DIC images indicating tissue motion polarity of microtumor. In the images, the dotted-line circle indicates the position of a spot.

FIG. 12 includes time-lapse DIC images when PCI-55 cells were cultured for 64 hours, using the cell culture substrate with Roughness (+) of 30 µm in spot diameter (hereinafter, referred to as a "cell culture substrate 1"). At the start of culture, PCI-55 cells were dispersed. It was then observed that as time elapsed, the PCI-55 cells aggregated, formed a cell mass on the spot, and became massive as a plurality of the cell masses were merged. FIG. 13 includes time-lapse DIC images focusing on one of the cell masses. The cell mass on a single spot was extending so as to crawl toward the adjacent spot. Thus, the tissue motion polarity of the cell mass was confirmed.

Figure 14:
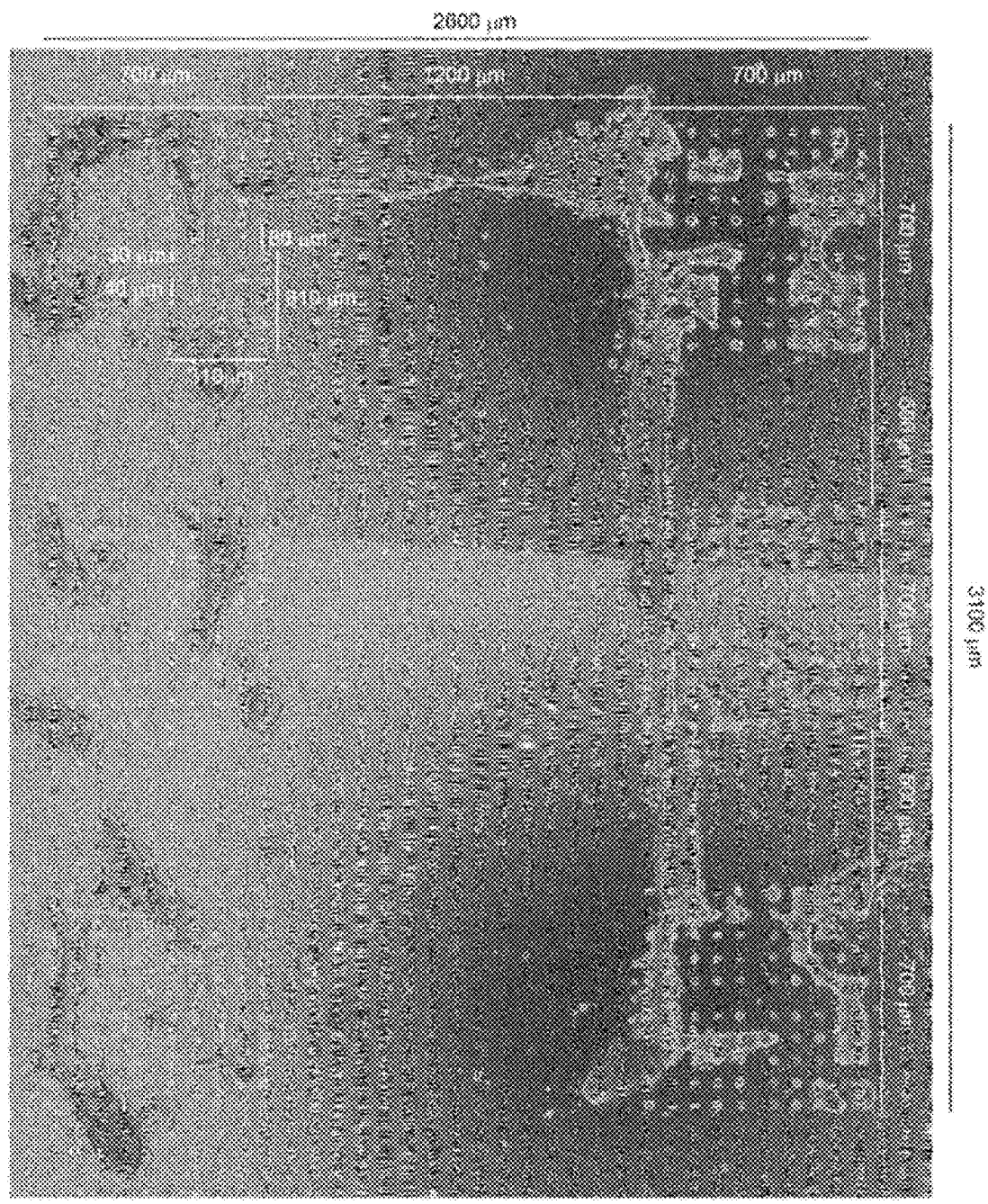
FIG. 14 is a wide view DIC image of microtumors cultured on the cell culture substrate 1 for 24 hours.

FIG. 14 is a wide view DIC image of PCI-55 cell mass cultured on the cell culture substrate 1. After being cultured for 24 hours, the cell mass has grown massive to over 3,000 µm in length in the area where the spots were present. It was also observed that the cell mass has stretched across an area of 1,200 µm in length where the spots were not present.

Next, by using four types of cell culture substrates with Roughness (+) having patterns in which 64 pieces, 36 pieces, 25 pieces, and 25 pieces of circular spots of 40 µm, 60 µm, 80 µm, and 100 µm in diameter respectively are arranged per 1 mm$^2$, PCI-55 cells were cultured overnight as the above. The proportions of the spot total areas occupying the surface areas of the cell culture substrates were each about 8.0%, about 10.2%, about 12.6%, and about 19.6%.

Figure 15:
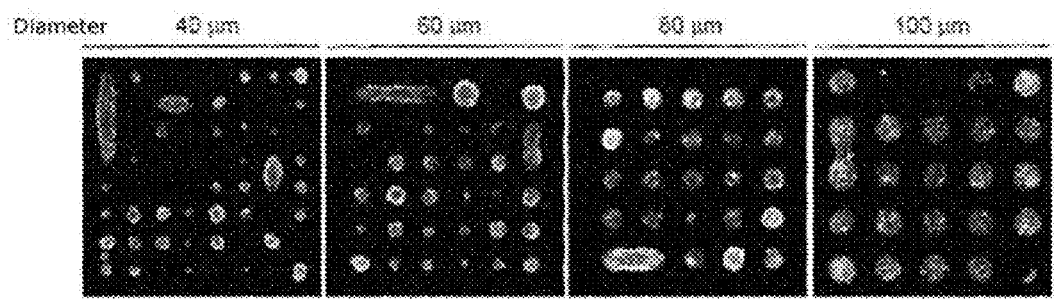
FIG. 15 includes fluorescence images (α-tubulin staining) of PCI-55 cells cultured on cell culture substrates with Roughness (+) of 40 μm, 60 μm, 80 μm, and 100 μm in spot diameter respectively.

After being cultured, the cell mass was fixed with paraformaldehyde, α-tubulin was stained using anti-α-tubulin antibody, and two-dimensional images were obtained using an all-in-one fluorescence microscope (BZ-X700, BZ-9000, KEYENCE). The formation of α-tubulin-positive cell mass stretching across two or more spots was identified in all the cell culture substrates (FIG. 15).

Similarly, PCI-55 cell mass stretching across two or more spots was also formed in the cell culture substrates with Roughness (+) having a pattern in which a single circular spot of 20 µm in diameter is arranged per 1 mm$^2$, and a pattern in which 81 pieces of circular spots of 100 µm in diameter are arranged per 1 mm$^2$ (data are not illustrated). The proportions of the spot total areas occupying the surface areas of these cell culture substrates were each about 0.03% and about 65%.

Figure 16:
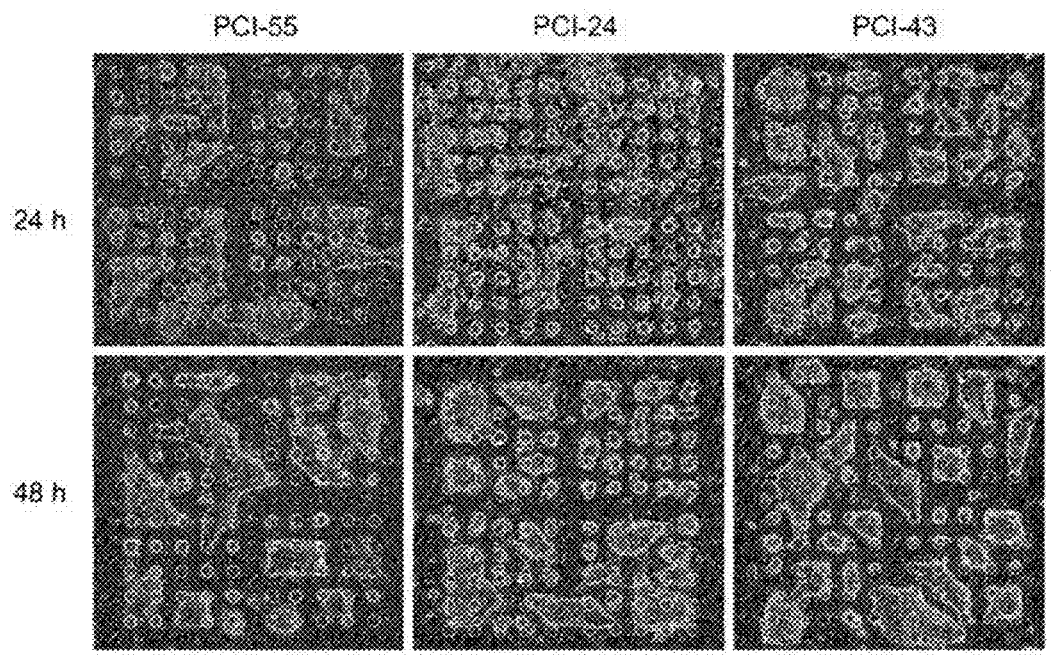
FIG. 16 includes transmission light images of KRAS-mutated human pancreatic ductal adenocarcinoma cell lines PCI-55, PCI-24, and PCI-43 cultured on the cell culture substrate 1 after being cultured for 24 hours and 48 hours.
Figure 17:
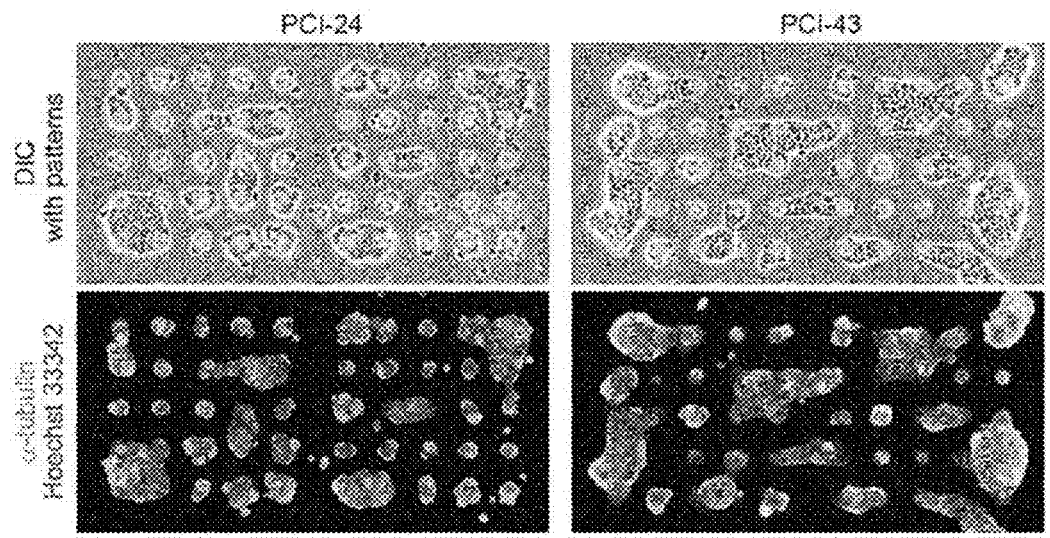
FIG. 17 includes DIC images and fluorescence images (merger of Hoechst 33342 and α-tubulin) of PCI-24 and PCI-43 that are fixed after being cultured on the cell culture substrate 1 and to which fluorescent immunostaining is performed.
Figure 18:
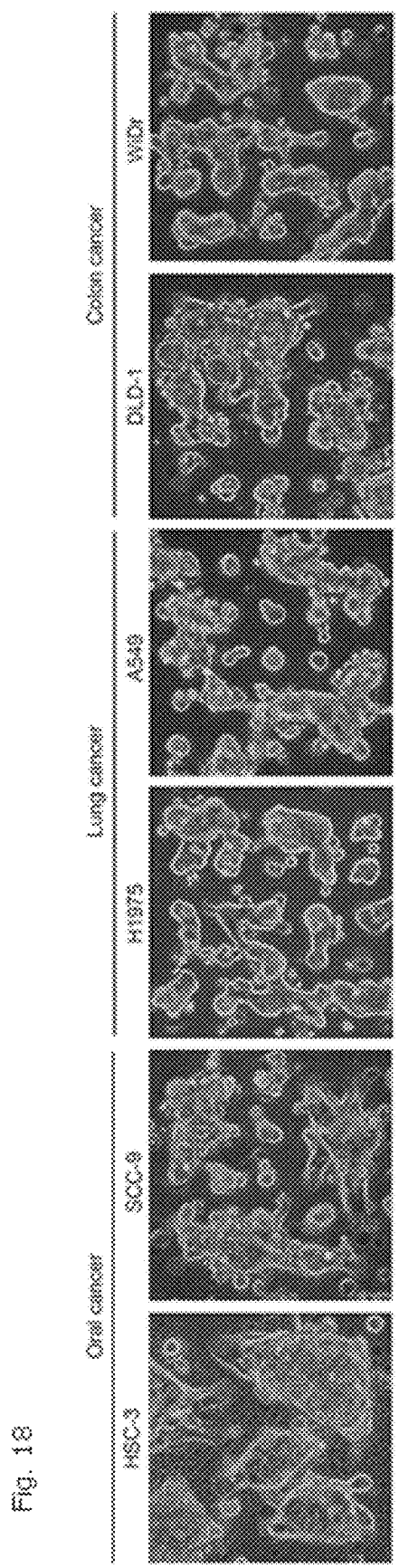
FIG. 18 includes DIC images of human lingual cancer cell lines HSC-3 and SCC-9, human lung cancer cell lines H1975 and A549, and human colon cancer cell lines DLD-1 and WiDr that are human epithelial cancer cell lines cultured on the cell culture substrate 1.

The formation of a cell mass was also observed in the other cancer cells. As examples, FIG. 16 to FIG. 18 illustrate images of cell masses formed from human pancreatic ductal adenocarcinoma cell lines PCI-24 and PCI-43, human lingual cancer cell lines HSC-3 and SCC-9, human lung cancer cell lines H1975 and A549, and human colon cancer cell lines DLD-1 and WiDr cultured on the cell culture substrate 1.

Given the above, it was proved that the cell culture substrates with spots of 20 to 100 µm in diameter that have an uneven structure on the surface urge the formation of non-spheroidal cancer cell mass that has morphological polarity and tissue motion polarity, that is self-organized, and that is anchorage-dependent. Hereinafter, in the examples, such a cell mass formed by adhesion onto the cell culture substrate is referred to as a microtumor.

Example 3

Morphological Structural Analysis of Microtumors and Comparison with Pancreatic Ductal Adenocarcinoma In Vivo After fixing the microtumors consisting of PCI-55 cells formed on the cell culture substrate 1 in Example 2 with paraformaldehyde, cell nucleus were stained using Hoechst 33342, actin was stained using phalloidin, and α-tubulin was stained using anti-α-tubulin antibody. For the stained microtumors, two-dimensional images were obtained using the all-in-one fluorescence microscope (BZ-X700, BZ-9000, KEYENCE), and three-dimensional images were obtained by a high-speed confocal microscope (Ti-E, Nikon), a high-speed spectral confocal system (A1R, Nikon), and image acquisition software (NIS-Elements, Nikon). The images were then analyzed.

Figure 19:
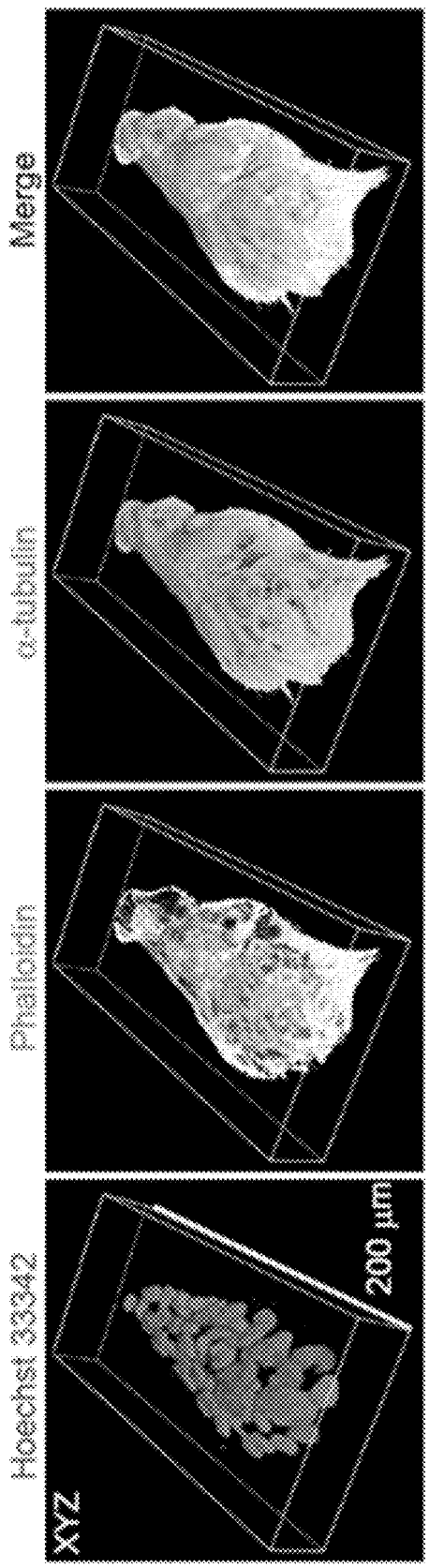
FIG. 19 includes three-dimensional fluorescence images (Hoechst 33342, phalloidin, and α-tubulin; and merger of Hoechst 33342, phalloidin, and α-tubulin) of PCI-55 microtumor cultured on the cell culture substrate 1.

FIG. 19 includes three-dimensional fluorescence images of a microtumor. A plurality of cell nuclei were contained in the microtumor, and expression of α-tubulin was observed around the entire surface of the microtumor. The membranous expression of α-tubulin was also confirmed in the other cell line (for example, FIG. 17), or when the cell culture substrate with different spot diameter was used (for example, FIG. 15).

Figure 20:
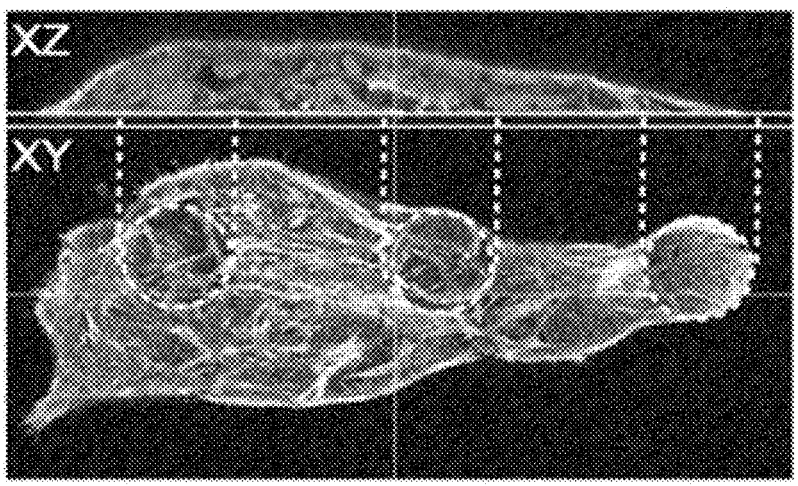
FIG. 20 includes fluorescence images (merger of Hoechst 33342, phalloidin, and α-tubulin) of sections of microtumor in the XY and XZ directions. In the image, the dotted-line circle indicates the position of a spot.

FIG. 20 includes fluorescence images of sections of the same microtumor in the XY and XZ directions. In the microtumor, portions considered to be vacuoles that are not stained with Hoechst 33342, phalloidin, or anti-α-tubulin antibody were present.

Figure 21:
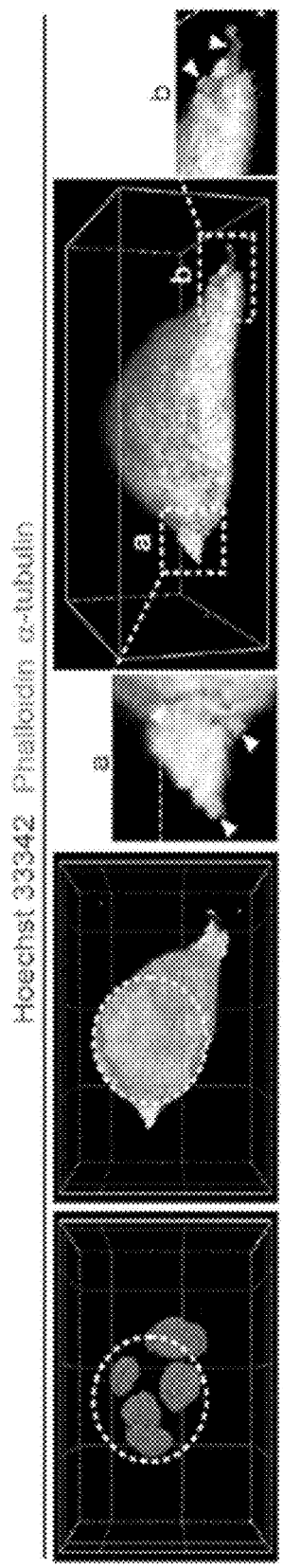
FIG. 21 includes upper surface views of three-dimensional fluorescence images (two images in the left) and perspective views of three-dimensional fluorescence images (three images in the right). The leftmost image is Hoechst 33342, and the other images are merger of Hoechst 33342, phalloidin, and α-tubulin. In the images, the dotted-line circle indicates the position of a spot, and the arrow head indicates cilia.

FIG. 21 includes fluorescence images of another microtumor. The expression of α-tubulin considered to be cilia was identified in a direction toward which the microtumor is estimated to extend (arrow head in FIG. 21).

Figure 22:
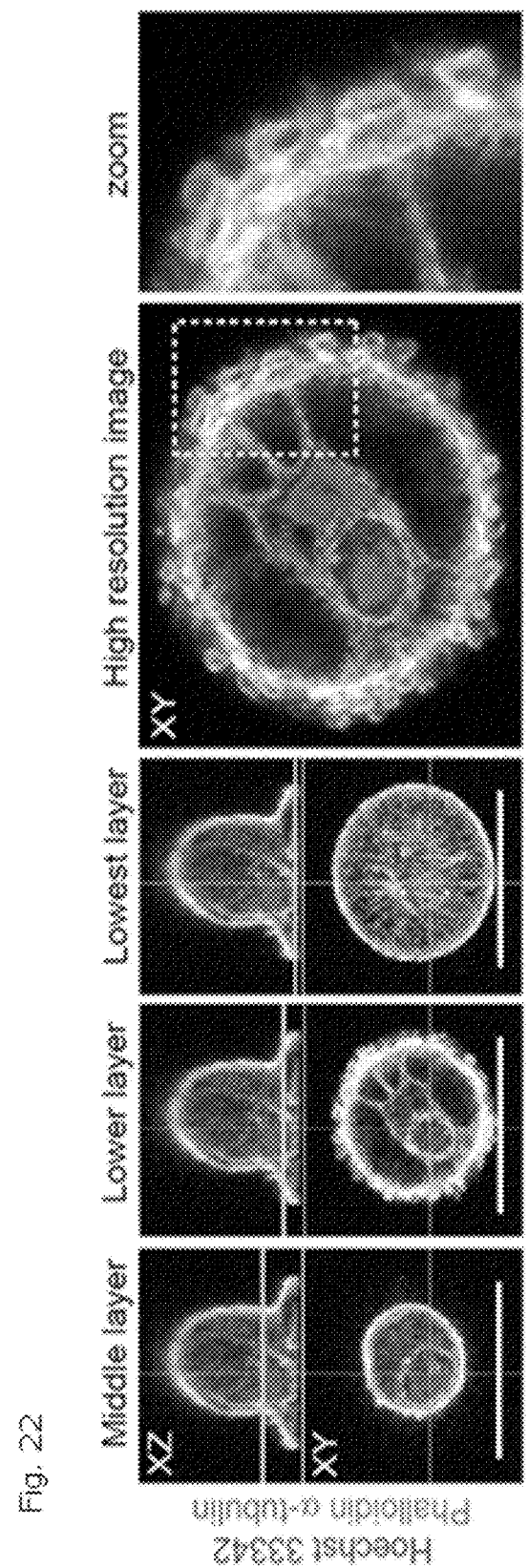
FIG. 22 includes fluorescence images (merger of Hoechst 33342, phalloidin, and α-tubulin) of sections of the lower layer of a papillary microtumor in the XY direction, being cut with a different Z-coordinate.

FIG. 22 includes fluorescence images of sections of the lower layer of another microtumor, which is self-organized into a papillary shape, in the XY direction, being cut with a different Z-coordinate. A number of ciliary bodies were formed on the lower layer surface portion of the papillary microtumor, and the induction of ciliogenesis was identified.

Figure 23:
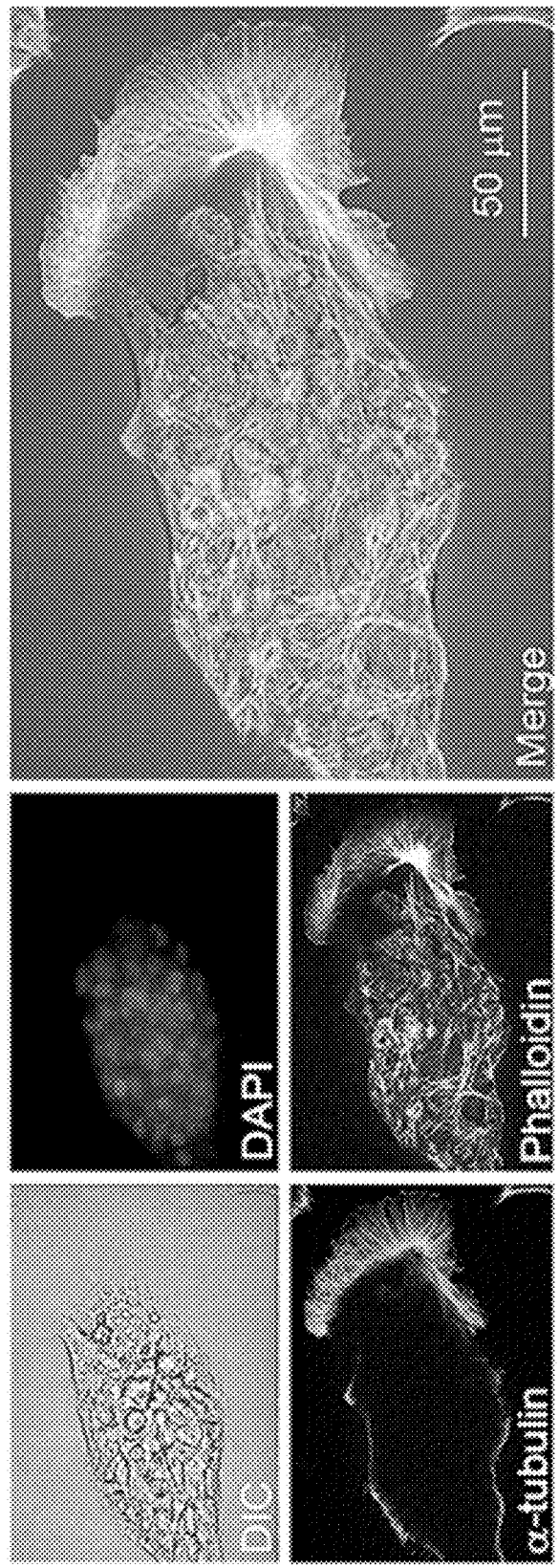
FIG. 23 includes DIC images and fluorescence images (DAPI, phalloidin, and α-tubulin; and merger of DAPI, phalloidin, and α-tubulin) of microtumor.

Moreover, the microtumor may integrally form lamellipodia (FIG. 23). It was found that the morphological polarity of the microtumor covered by membranous expression of α-tubulin is very close to that of a single cell.

Figure 24:
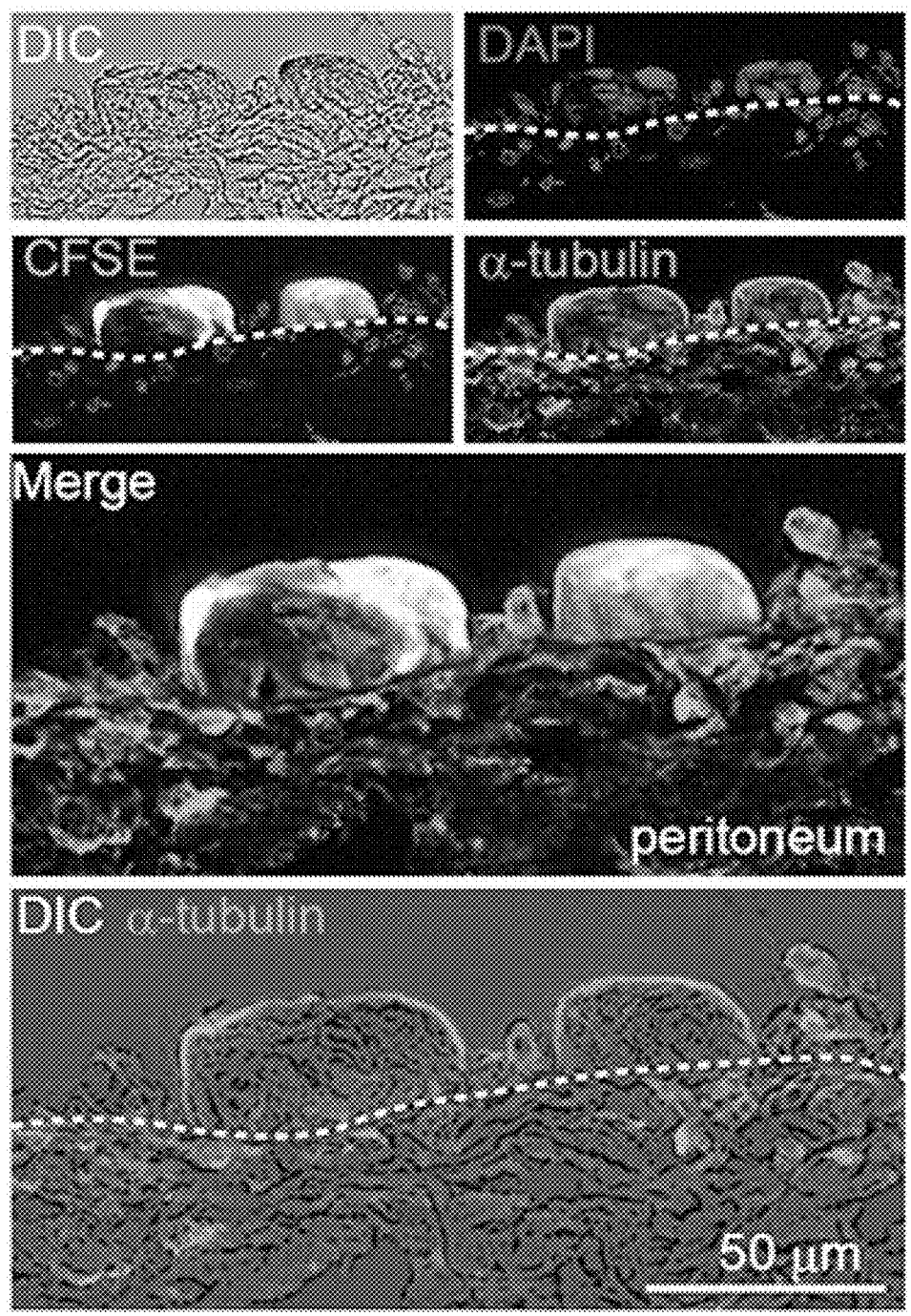
FIG. 24 includes DIC images and fluorescence images (DAPI, CFSE, and α-tubulin; and merger of DAPI, CFSE, and α-tubulin) of slices of peritoneal tissues from mouse intraperitoneally inoculated with PCI-55 cells.

Next, whether the phenomenon of membranous expression of α-tubulin described above also occurs in vivo was examined. A mixture of CFSE-labeled PCI-55 cells and unlabeled PCI-55 cells (5×10$^6$ cells each) suspended in 200 µL of PBS was administered intraperitoneally into six-to-eight-week old male C.B-17/Icr-scid/scidJcl mouse (CLEA, Japan). FIG. 24 is stained images of mouse peritoneal tissues three days after the administration. The membranous expression of α-tubulin was also observed on the microtumor formed by PCI-55 cells colonized on the mouse peritoneum.

Figure 25:
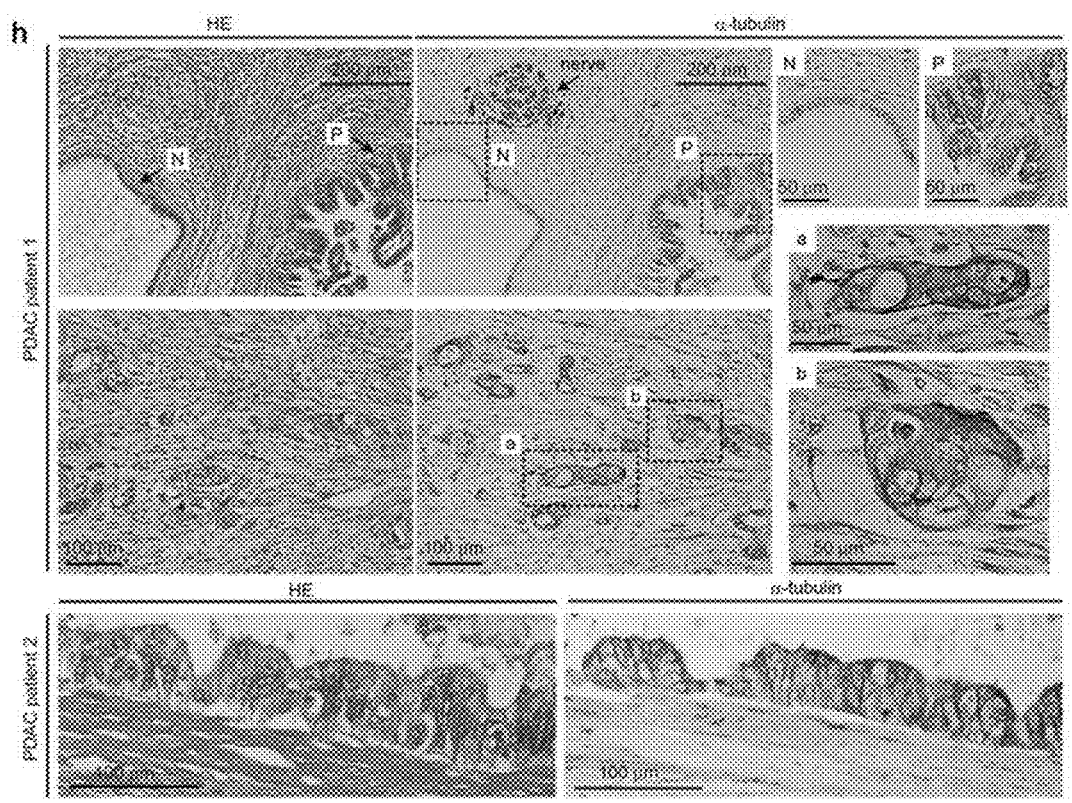
FIG. 25 includes hematoxylin-eosin stained images and α-tubulin immunostained images of tissue specimens of two cases of pancreatic ductal adenocarcinoma patients. N indicates a portion of normal pancreatic ductal epithelium, and P indicates a lesion site of malignantly transformed pancreatic ductal epithelium.

FIG. 25 includes hematoxylin-eosin stained images and α-tubulin immunostained images of specimens of two cases of pancreatic ductal adenocarcinoma patients. In the lesion site of malignantly transformed pancreatic ductal epithelium indicated by P, membranous expression of α-tubulin (estimated to be microtubule) was observed. However, membranous expression of α-tubulin was hardly observed in the normal pancreatic ductal epithelium portion indicated by N. Moreover, with an increase in malignancy of deformed cells and deformed structure, particularly in the lesion sites of pancreatic intraepithelial neoplasia (PDAC patient 2 of the lowest row in FIG. 25) and infiltrative pancreatic ductal adenocarcinoma, the membranous expression of α-tubulin tended to increase.

Given the above, it was proved that the membranous expression of α-tubulin around the surface of the microtumors formed on the cell culture substrate is a phenomenon also observed in vivo, and the microtumors will be a model for pancreatic ductal adenocarcinoma in a living body.

Example 4

Analysis on Entosis and Cell-in-Cell Structure in Microtumors

Figure 26:
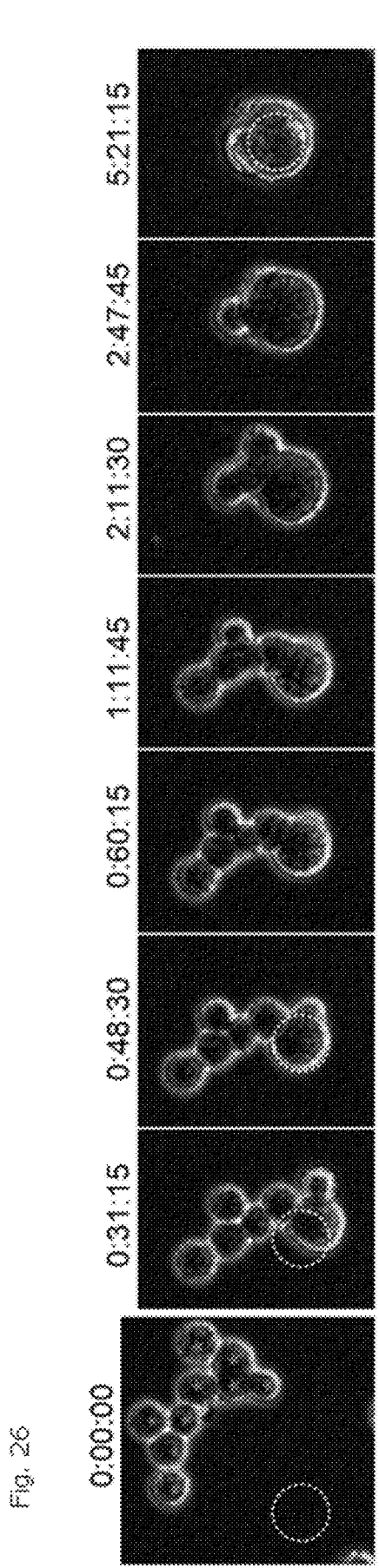
FIG. 26 includes time-lapse DIC images indicating states of an assembly of cells adhering to a spot while entosis is occurring. In the images, the dotted-line circle indicates the position of a spot.
Figure 27:
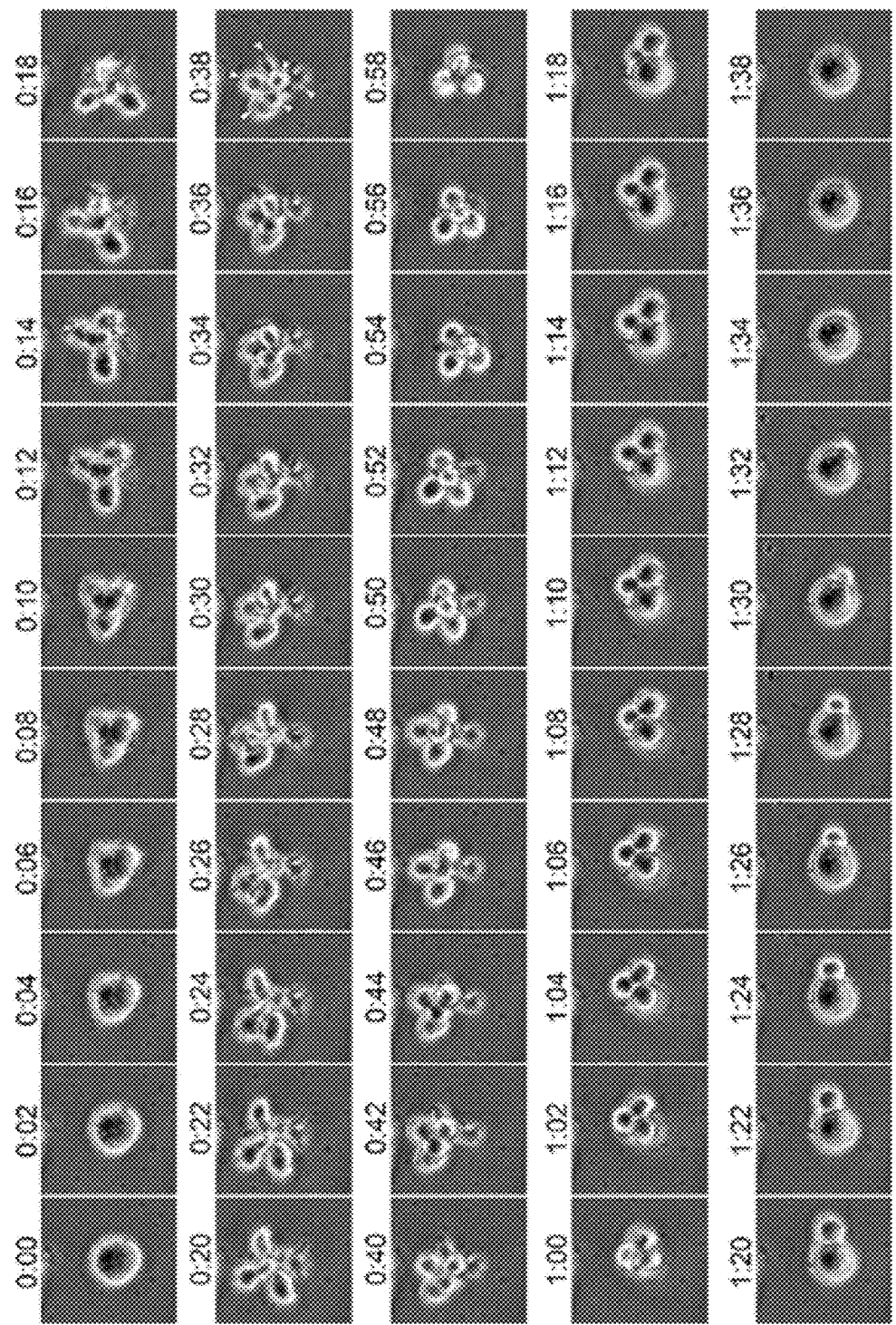
FIG. 27 includes time-lapse DIC images indicating reversible entosis in microtumor.

A state of PCI-55 cells cultured on the cell culture substrate 1 in Example 2 adhering to the substrate was observed by the DIC. The chained assembly consisting of nine cells in FIG. 26 was settled on a spot while going into a phenomenon called entosis in which a cell is incorporated into another cell, and became a single microtumor in the end. A state of the cell being incorporated into another cell by entosis, going out the cell again, returning to an assembly of a plurality of cells, and then being incorporated into another cell again by entosis was also observed (FIG. 27). It was considered that entosis in microtumor is reversible.

Figure 28:
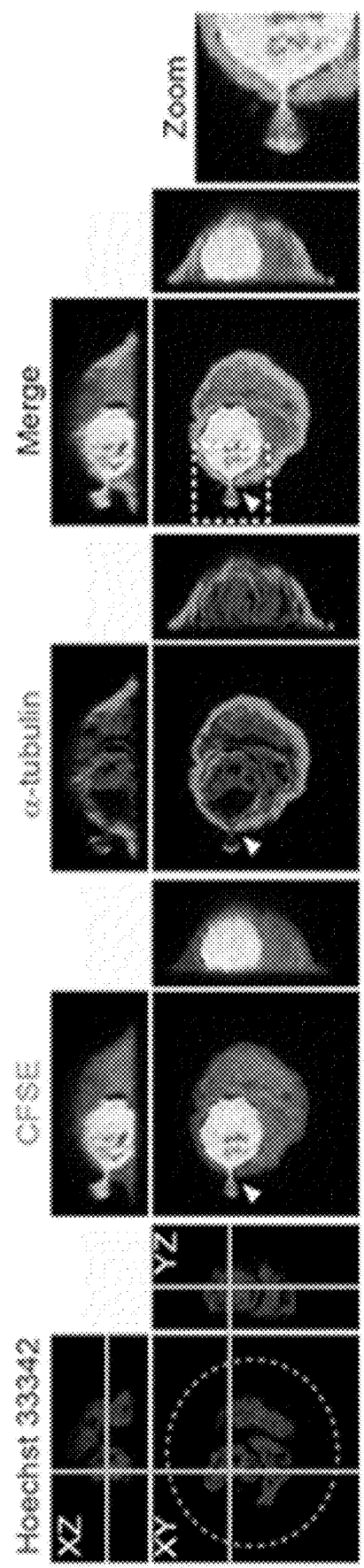
FIG. 28 includes fluorescence images (Hoechst 33342, CFSE, and α-tubulin; and merger of Hoechst 33342, CFSE, and α-tubulin) of sections of microtumor in the XY, YZ, and XZ directions. In the images, the arrow head indicates a portion where a cell penetrates through a cell membrane of another cell due to entosis.

Next, PCI-55 cells labeled with CFSE were seeded on the cell culture substrate 1. A microtumor was formed as in Example 2, and was observed by a fluorescence microscope. The fluorescence intensity of the CFSE-labeled cells is reduced to half by a single cell division. Consequently, the fluorescence intensity is changed depending on the number of times cell division has occurred. This microtumor contains three cells therein, and a state of a single strong fluorescent cell among the cells penetrating through the cell membrane of the microtumor formed of weak fluorescent cells was observed (FIG. 28).

Figure 29:
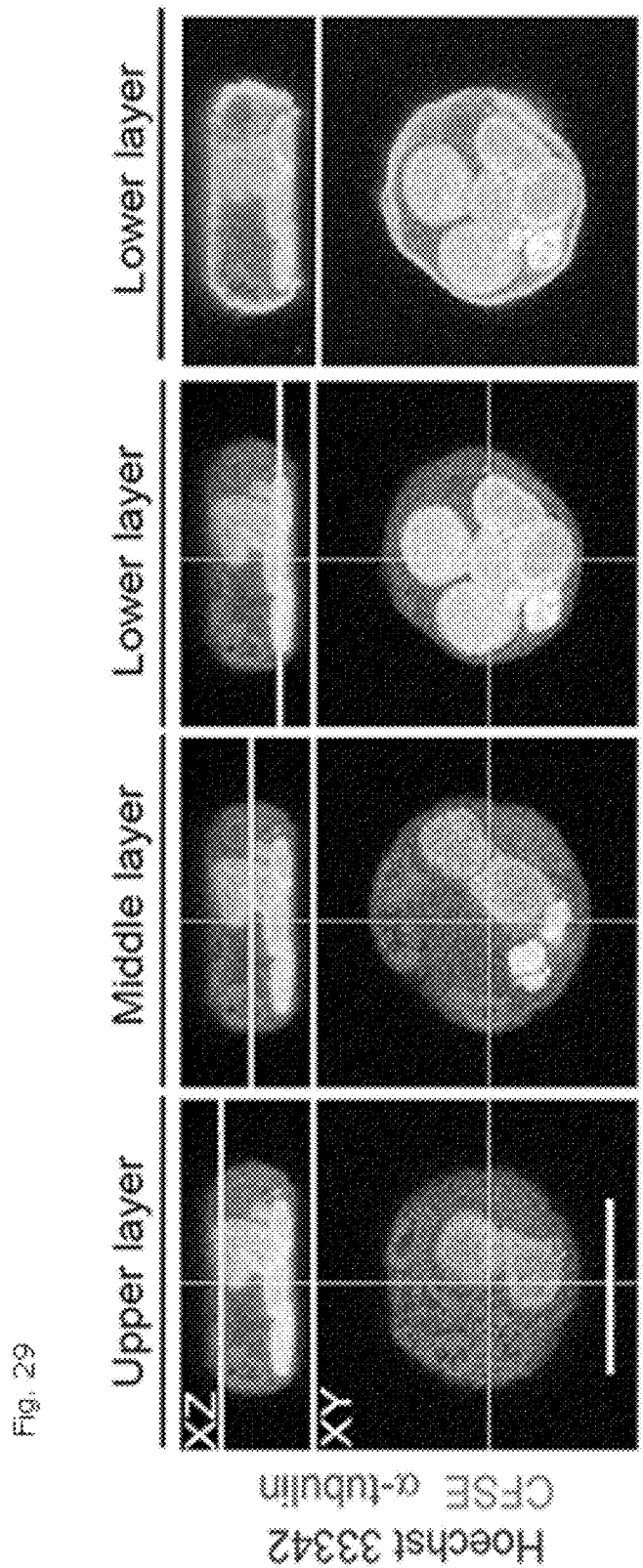
FIG. 29 includes fluorescence images (merger of Hoechst 33342, phalloidin, and α-tubulin) of sections of microtumor in the XY direction, being cut with a different Z-coordinate.

FIG. 29 includes fluorescence images of another microtumor formed of CFSE-labeled PCI-55 cells. This microtumor had a cell-in-cell structure in which six strong fluorescent cells were contained in a weak fluorescent cell.

Such cell-in-cell structure formed by entosis was also observed in a specimen of a case of pancreatic ductal adenocarcinoma (portions a and b in FIG. 25).

Figure 30:
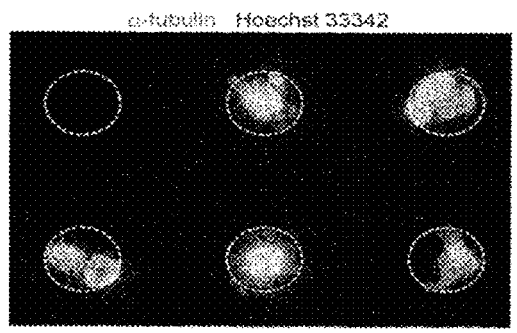
FIG. 30 is a fluorescence image (merger of Hoechst 33342 and α-tubulin) of normal human embryonic pancreas-derived cell line 1C3IKEI, cultured on the cell culture substrate 1. In the image, the dotted-line circle indicates the position of a spot.
Figure 31:
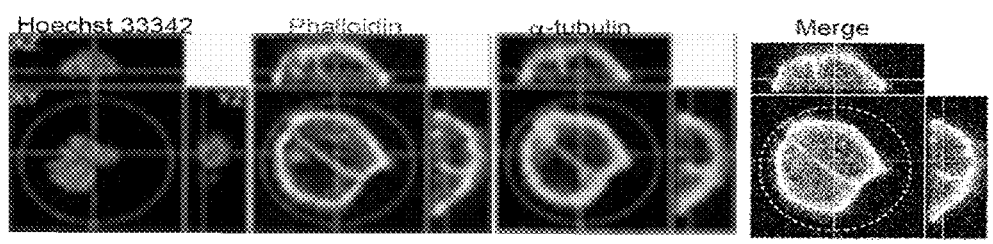
FIG. 31 includes fluorescence images (Hoechst 33342, phalloidin, and α-tubulin; and merger of Hoechst 33342, phalloidin, and α-tubulin) of sections of 1C3KEI cells after being cultured in the XY, YZ, and XZ directions.

By contrast, when the normal human embryonic pancreas-derived cell line 1C3IKEI was cultured on the cell culture substrate 1, the membranous expression of α-tubulin on the cell mass surface and the cell-in-cell structure were not observed (FIG. 30 and FIG. 31).

Given the above, the microtumor formed on the cell culture substrate had a cell-in-cell structure by entosis, and this structure was also observed in a pancreatic ductal adenocarcinoma patient. Consequently, it was proved that the microtumor will be a model for pancreatic ductal adenocarcinoma in vivo.

Example 5

Analysis on Engulfment of Dead Cells and Immune Evasion of Microtumors

Figure 32:
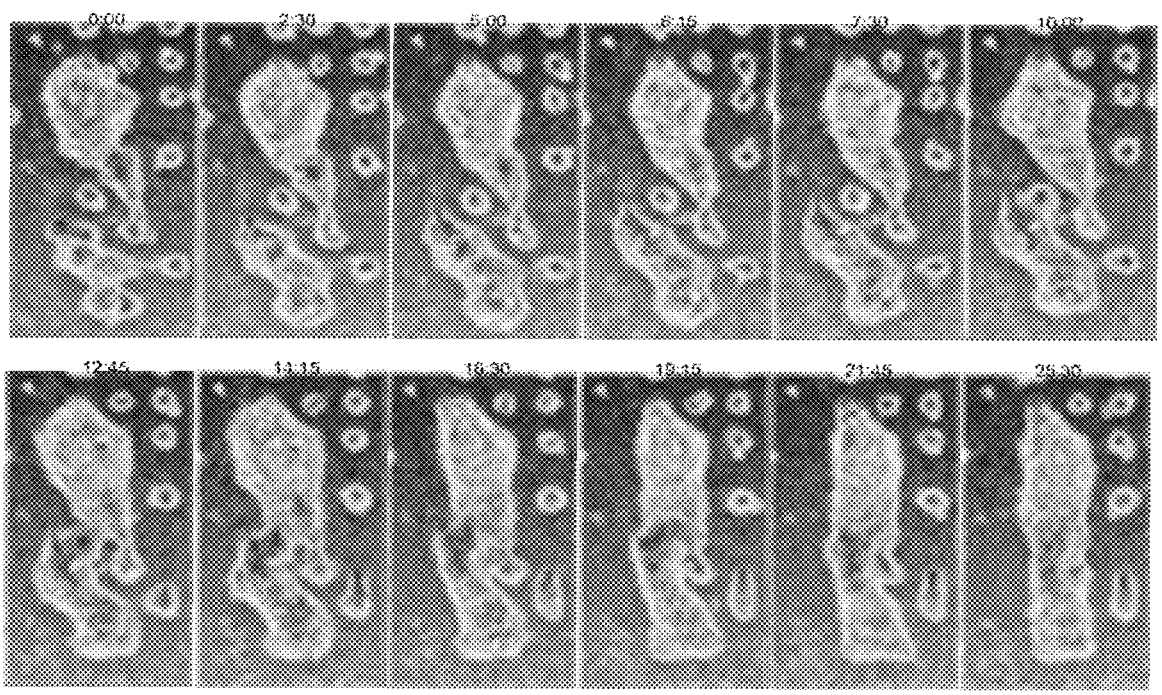
FIG. 32 includes time-lapse DIC images of states of microtumors incorporating cell debris. The arrow heads (upper left and center left) at two locations in the images indicate the positions of engulfed debris.

A state of the microtumor consisting of PCI-55 cells formed on the cell culture substrate 1 in Example 2 incorporating debris was observed by acquiring time-lapse DIC images. The microtumor was actively catching debris using filipodia and lamellipodia (arrow head in FIG. 32).

Figure 33:
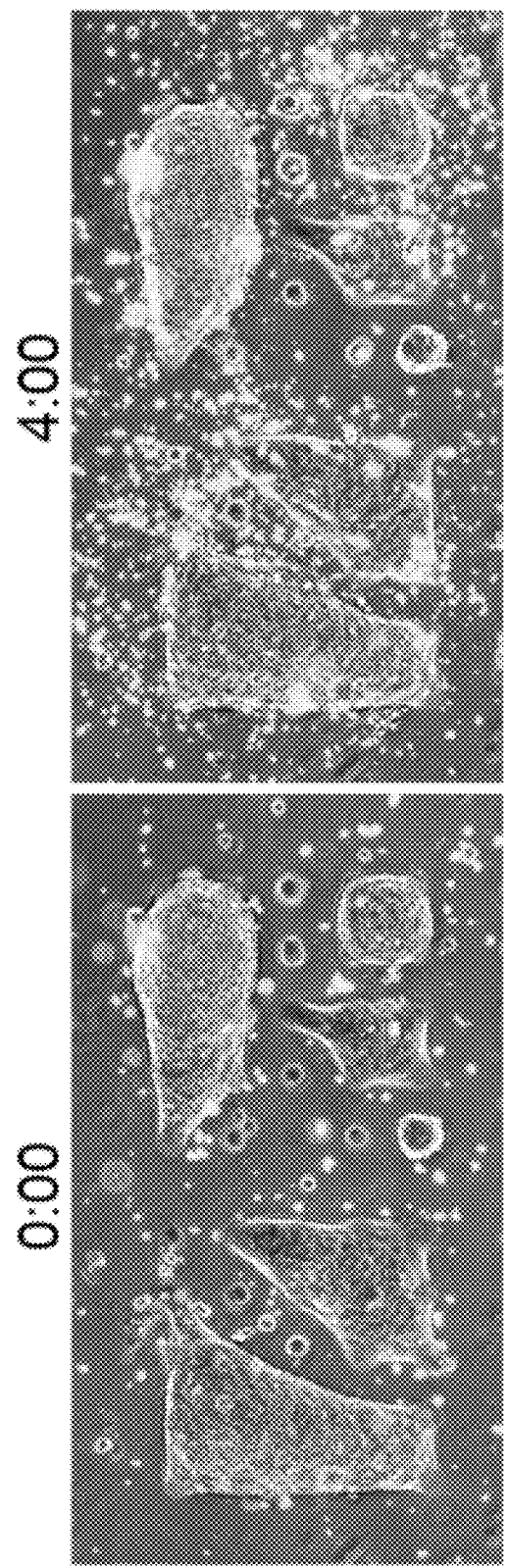
FIG. 33 includes time-lapse images obtained by merging DIC and fluorescence images (CFSE and ethidium homodimer (EthD)) of microtumors that are made to coexist with green-fluorescent nanobeads.

Moreover, a flow of culture medium was observed by adding green-fluorescent nanobeads to the culture medium of microtumor (FIG. 33). In four hours after the nanobeads were added, many nanobeads were collected around the microtumor. Consequently, it was considered that the microtumor has a powerful suction force.

Next, by adding PCI-55 dead cell debris to a culture medium, a state of microtumor engulfing dead cells was observed. The dead cell debris was prepared as follows. PCI-55 cells ($5 \times 10^5$ cells) were cultured in 60 mm tissue culture dish for 24 hours, and the cells were irradiated with ultraviolet light (UV) at an intensity of 250 mJ/cm$^2$ with Bio-Rad GS Gene Linker (Bio-Rad). The UV-irradiated monolayer-cultured PCI-55 cells were washed, and cell death was induced by adding 3 mL of DMEM and incubating for three hours. The dead cells were suspended in a culture medium using a cell scraper. The culture medium containing dead cell debris was added to a microtumor consisting of PCI-55 cells that were formed on the cell culture substrate 1 by being cultured for 24 hours. Live imaging analysis was then performed by further adding Annexin V (25 μL) and EthD-1 (2 μL). After fixing the microtumor with paraformaldehyde and staining nucleus, three-dimensional (3D) imaging analysis was performed using the confocal.

Figure 34:
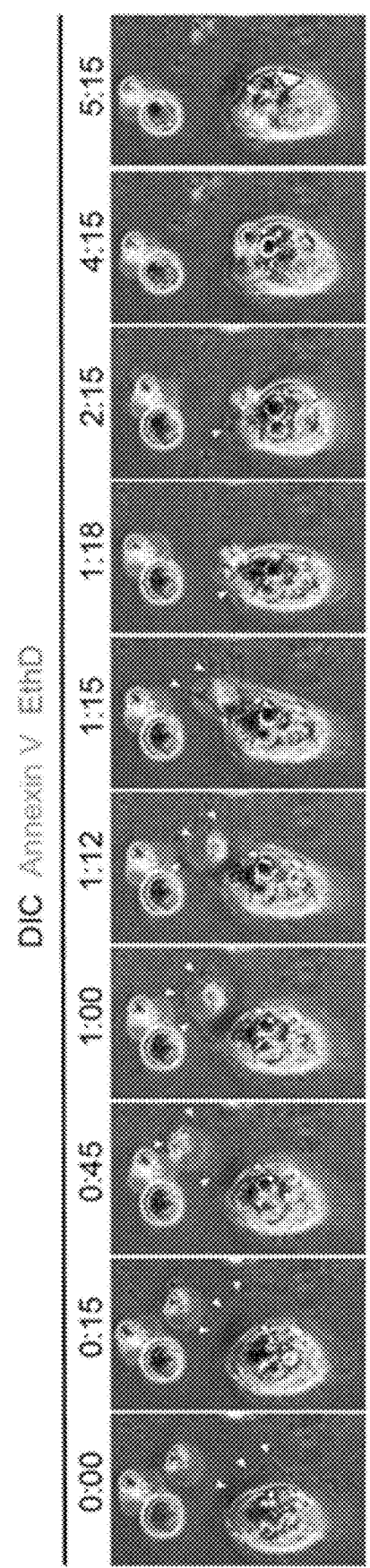
FIG. 34 includes time-lapse images obtained by merging DIC and fluorescence images (Annexin V and EthD) of states of microtumor engulfing dead cells. In the images, the arrow head indicates the position of lamellipodia of the microtumor.
Figure 35:
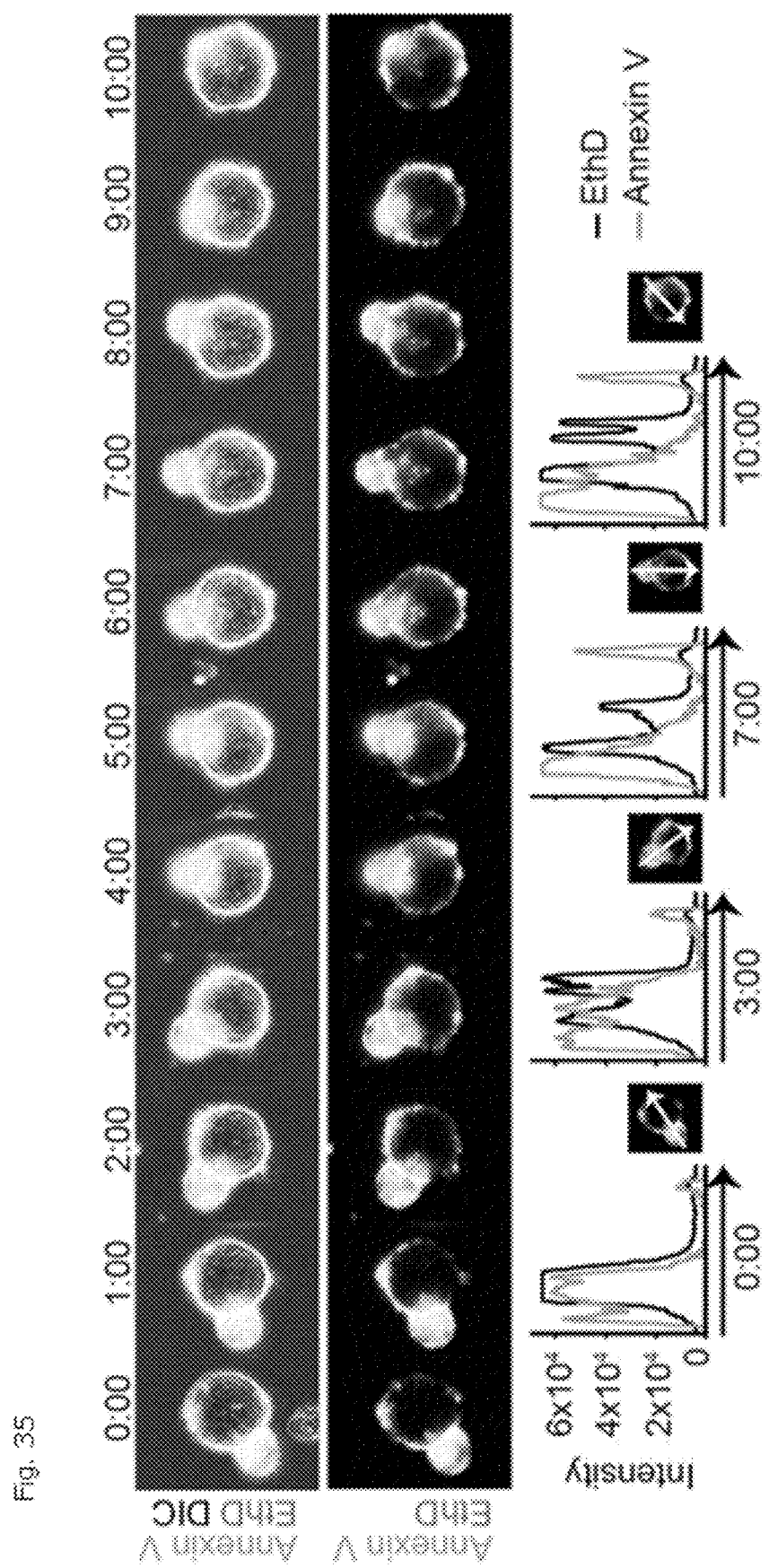
FIG. 35 includes time-lapse images (upper row) obtained by merging DIC and fluorescence images (Annexin V and EthD) and time-lapse fluorescence images (middle row) of states of microtumor engulfing a dead cell, and graphs (bottom row) of fluorescence intensity distribution in the microtumor at each time point.
Figure 36:
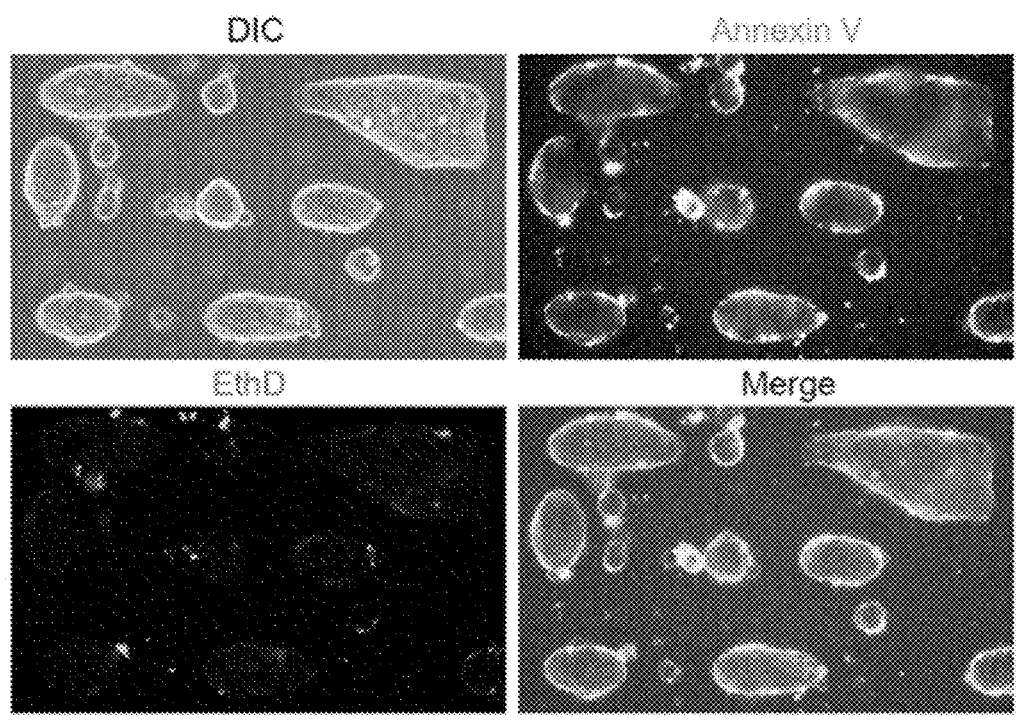
FIG. 36 includes DIC images and fluorescence images (Annexin V and EthD) of live microtumors after being cultured for 24 hours.

By using massive lamellipodia (arrow head in FIG. 34), the microtumor caught the dead cells and the debris thereof, and incorporated them into the microtumor. Moreover, when the dead cells were incorporated into the microtumor, EthD-1 was incorporated in the microtumor, but Annexin V was accumulated on the surface of the microtumor (FIG. 35 and FIG. 36).

Figure 37:
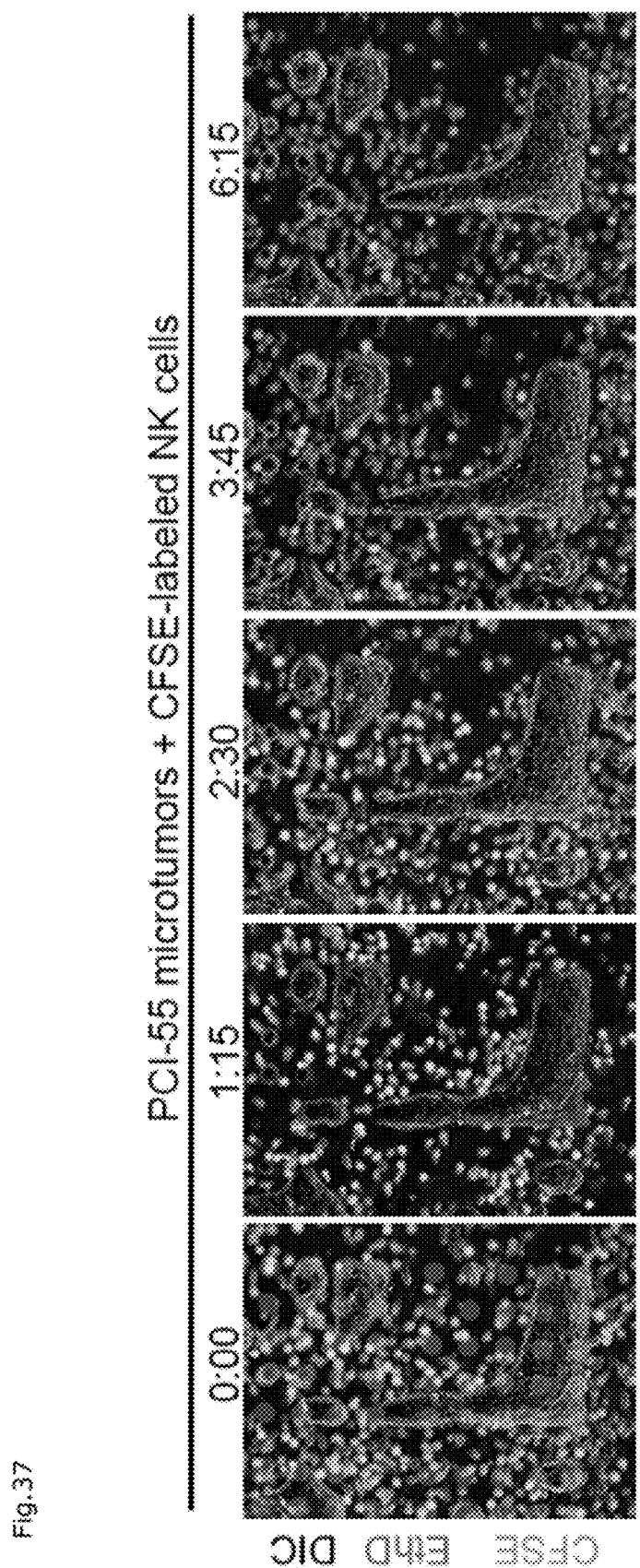
FIG. 37 includes time-lapse images obtained by merging DIC and fluorescence images (CFSE and EthD) of microtumors cocultured with human natural killer (NK) cell line KHYG-1 cells.

Furthermore, $3 \times 10^6$ of human NK cell line KHYG-1 were added to the microtumor formed by culturing $3 \times 10^6$ of PCI-55 cells on the cell culture substrate 1 at 37 degrees Celsius overnight, and cocultured for six hours and 15 minutes, while acquiring time-lapse DIC images. A state of KHYG-1 cells not attacking the microtumor, but being killed by fratricide was observed (FIG. 37).

Given the above, it was confirmed that by incorporating or attracting the dead cells, the microtumor exhibits Annexin V positive (in other words, phosphatidylserine positive) and/or EthD-1 positive that is a conventional dead cell phenotype. Moreover, it was suggested that the microtumor the external surface of which is accumulated with phosphatidylserine derived from dead cells is misrecognized as non-viable tissues by immune cells, and escape attacks from the immune system.

Example 6

Culturing Microtumors on Conventional Culture Substrate

Figure 38:
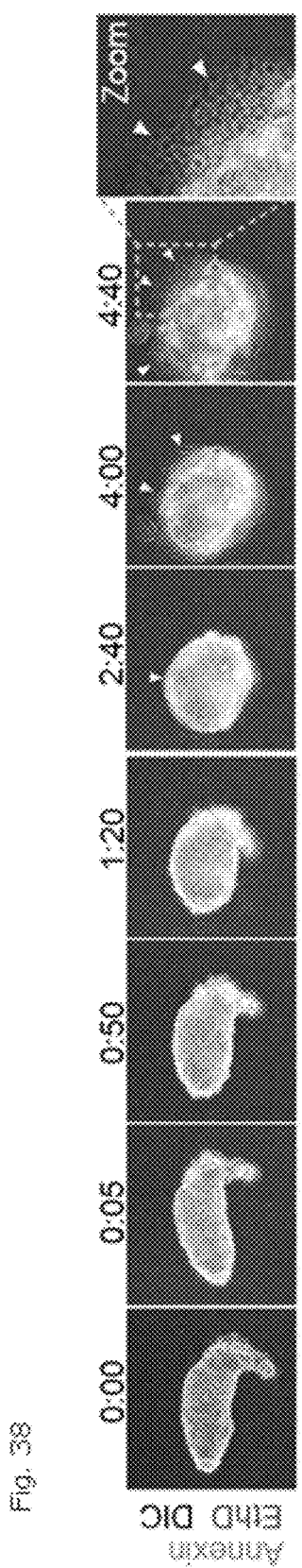
FIG. 38 includes time-lapse images obtained by merging DIC and fluorescence images of microtumor moved to be cultured in a normal cell culture dish after being cultured on the cell culture substrate 1.

When the microtumor made to coexist with dead cells in Example 5 was collected and cultured on a conventional cell culture dish (Falcon (registered trademark) cell culture dish 35×10 mm easy-grip style, Falcon), the morphological polarity of the microtumor was reduced, and the accumulation of Annexin V on the surface was also lost (FIG. 38). Given the above, it was presumed that the microtumor needs to be cultured on the cell culture substrate having a three-dimensional structure to be an anchorage, to survive while maintaining the characteristics of the microtumor.

Example 7

Growth of Microtumors Having Engulfed Dead Cells

Figure 39:
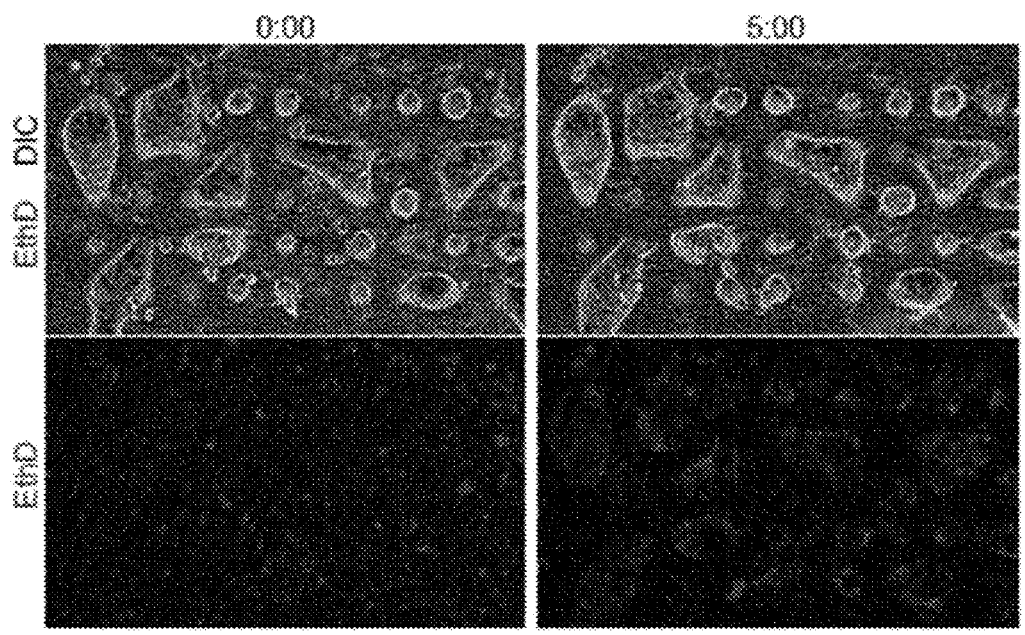
FIG. 39 includes time-lapse images obtained by merging DIC and fluorescence images (EthD) of microtumors made to coexist with PCI-55 dead cells.
Figure 40:
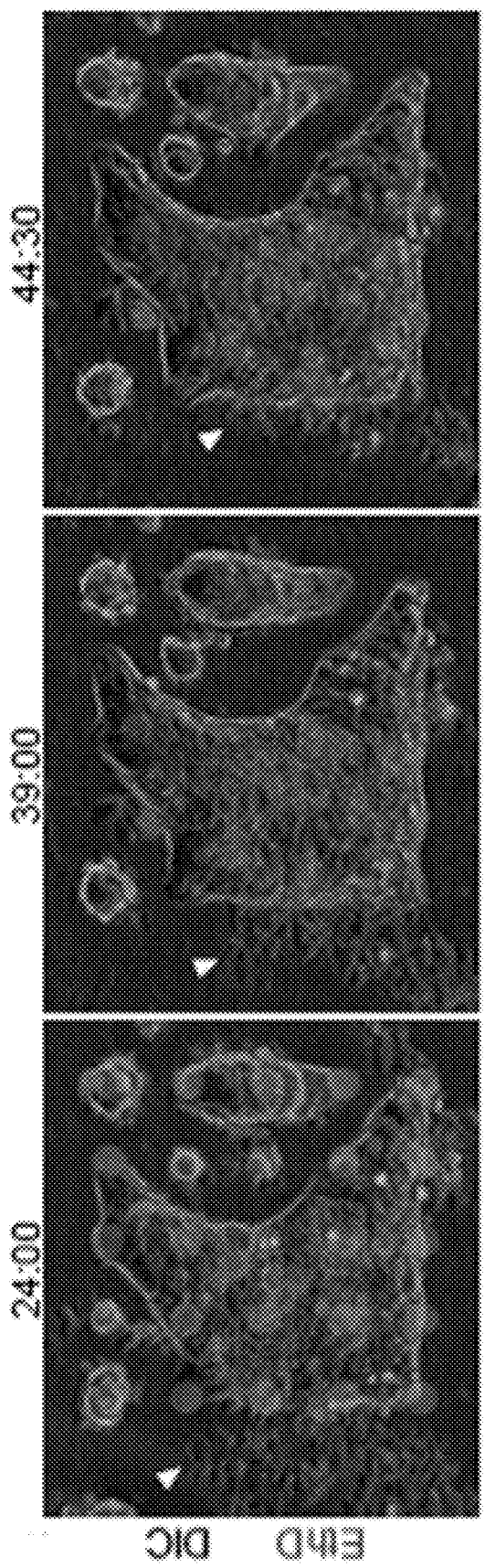
FIG. 40 includes time-lapse images obtained by merging DIC and fluorescence images (EthD) of microtumors made to coexist with dead cells. In the images, the arrow head indicates the position of the engulfed dead-cell debris.
Figure 41:
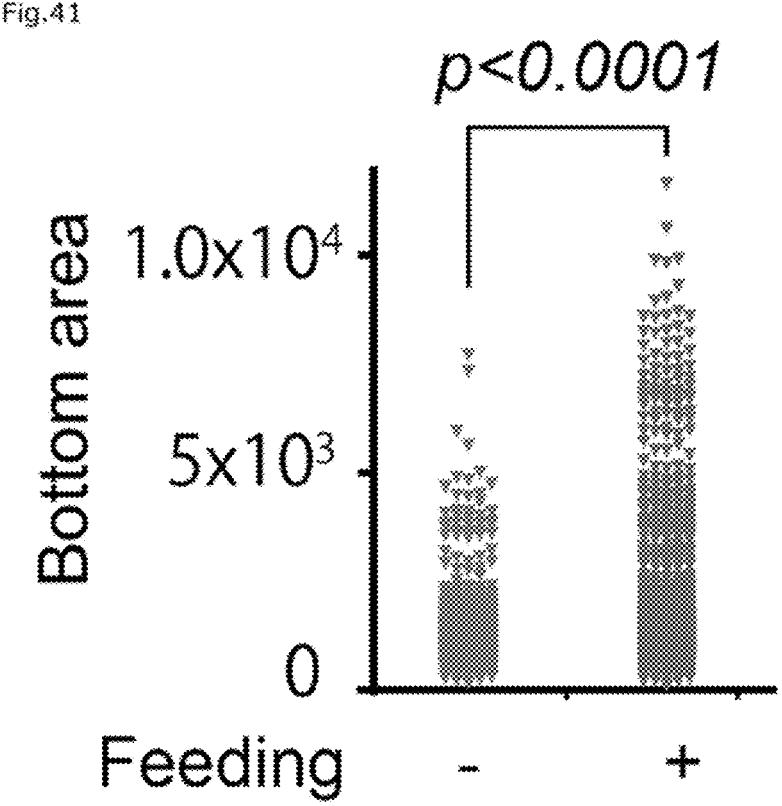
FIG. 41 is a scatter diagram illustrating an increase in the bottom area of microtumors when dead cells are added.

A state of the microtumor made to coexist with dead cells in Example 5 incorporating the dead cells was observed by acquiring time-lapse DIC images. The microtumor engulfed a number of dead cells, and incorporated a large amount of EthD-1 therein (FIG. 39 and FIG. 40). Moreover, it was confirmed that the bottom area of the microtumor 48 hours after the dead cells were added was significantly increased than that of the microtumor not added with dead cells, and the tumor size was increased (FIG. 41). Given the above, it was proved that the microtumor engulfs dead cells and grows as if the microtumor is a single cell.

Example 8

Demonstration of Incorporation of Nucleoside Derived from Foreign Dead Cells in Microtumors Nucleoside metabolism in a microtumor consisting of PCI-55 cells formed on the cell culture substrate 1 in Example 2 was examined using dead cells that had previously incorporated thymidine nucleoside analog 5-ethynyl-2'-deoxyuridine (EdU) (EdU dead cells). The EdU dead cells were prepared similar to that in Example 5, except that PCI-55 cells were cultured in 10 µM EdU-added culture medium. After adding the EdU dead cells to the microtumor consisting of CSFE-labeled PCI-55 cells and culturing the microtumor, the microtumor was fixed with paraformaldehyde, and EdU was detected by Click-iT (registered trademark) Plus assay.

Figure 42:
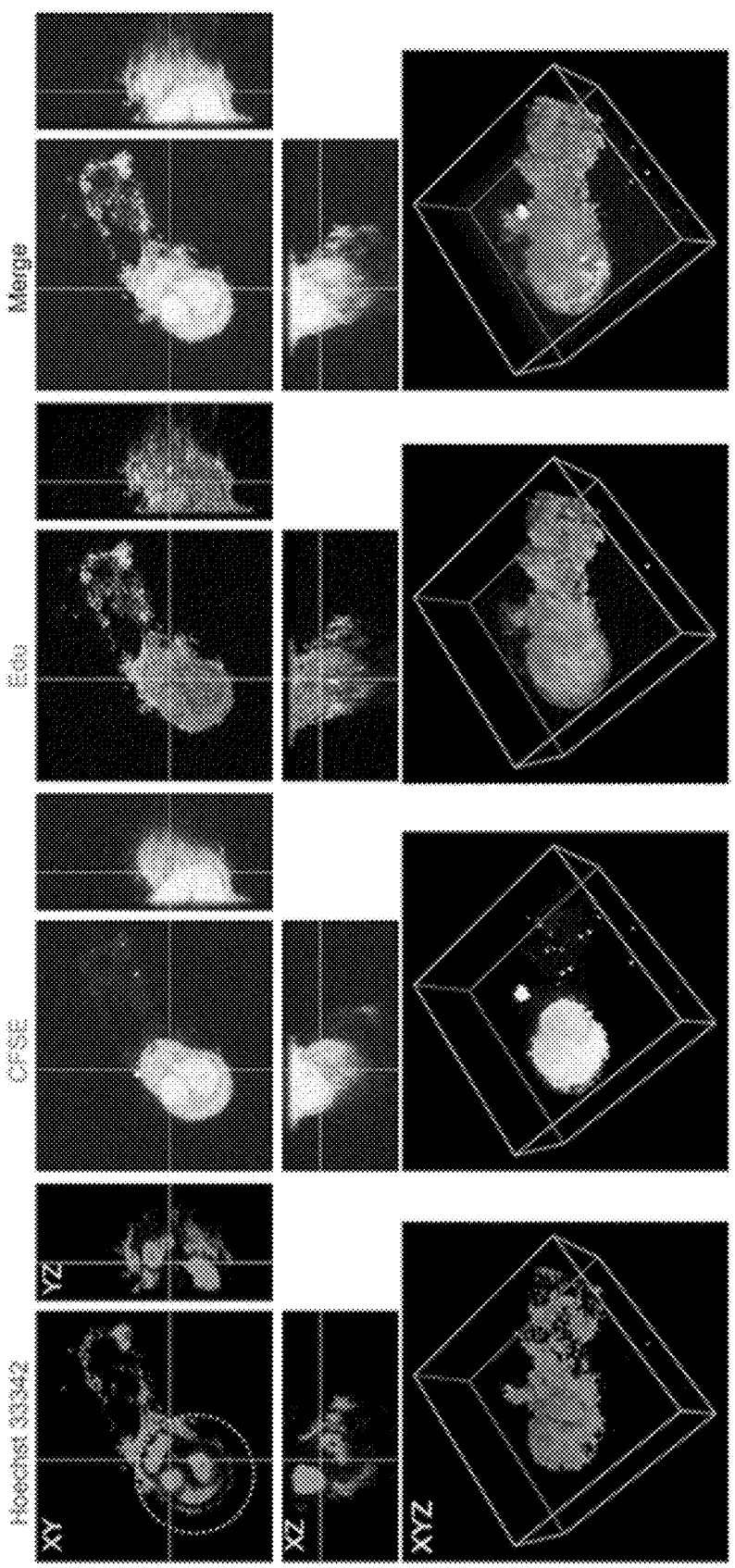
FIG. 42 includes sectional views in the XY, YZ, and XZ directions and three-dimensional fluorescence images (Hoechst 33342, CSFE, and EdU; and merger of Hoechst 33342, CSFE, and EdU) of CFSE-labeled microtumor made to coexist with dead cells that have incorporated 5-ethynyl-2'-deoxyuridine (EdU) being a thymidine nucleoside analog.
Figure 43:
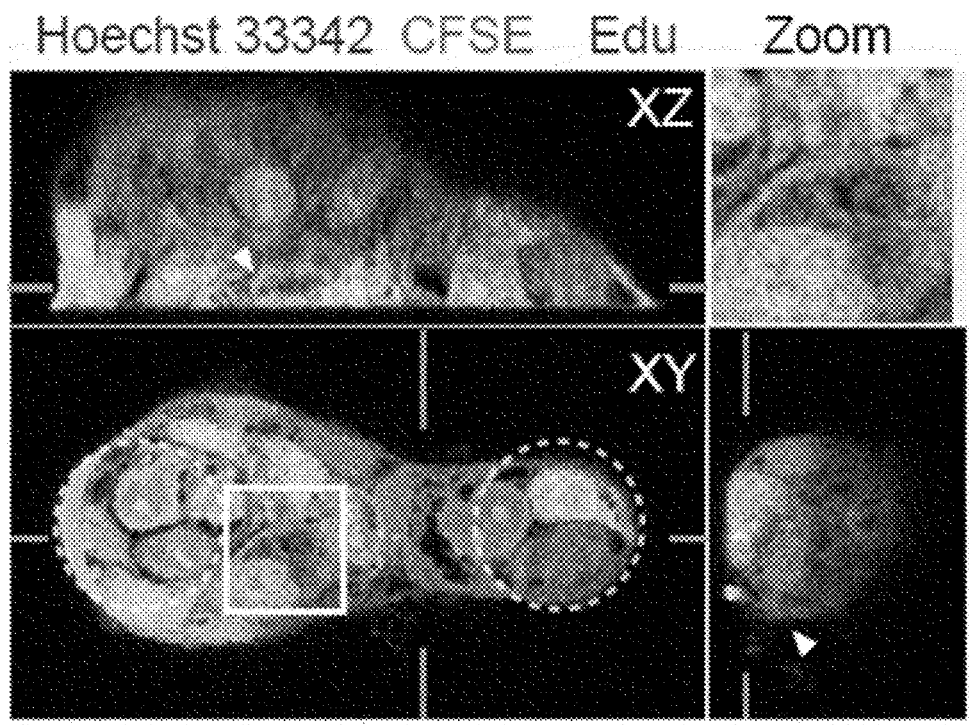
FIG. 43 includes fluorescence images (merger of Hoechst 33342, CSFE, and EdU) of sections of CFSE-labeled microtumor made to coexist with dead cells that had previously incorporated EdU, in the XY, YZ, and XZ directions. In the images, the dotted-line circle indicates the position of a spot, and the enlarged image and the arrow head indicate the localization of EdU incorporated in the microtumor.
Figure 44:
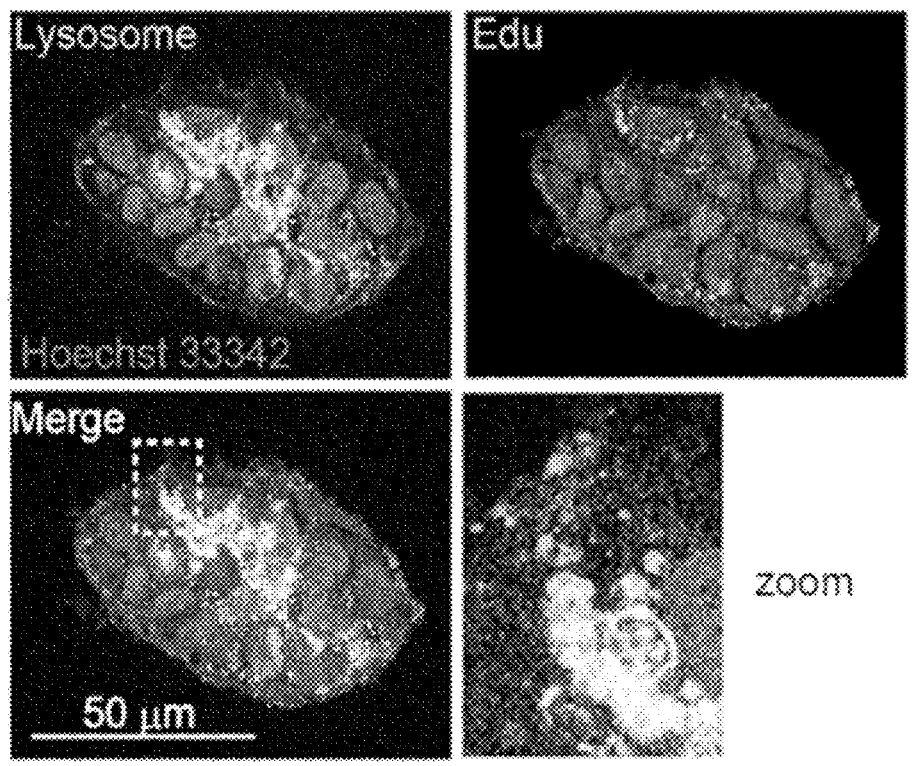
FIG. 44 includes fluorescence images (merger of Hoechst 33342 and lysosome; EDU; and merger of Hoechst 33342, lysosome, and EDU) of a section of microtumor added with dead cells that has incorporated EdU in the XY direction.
Figure 45:
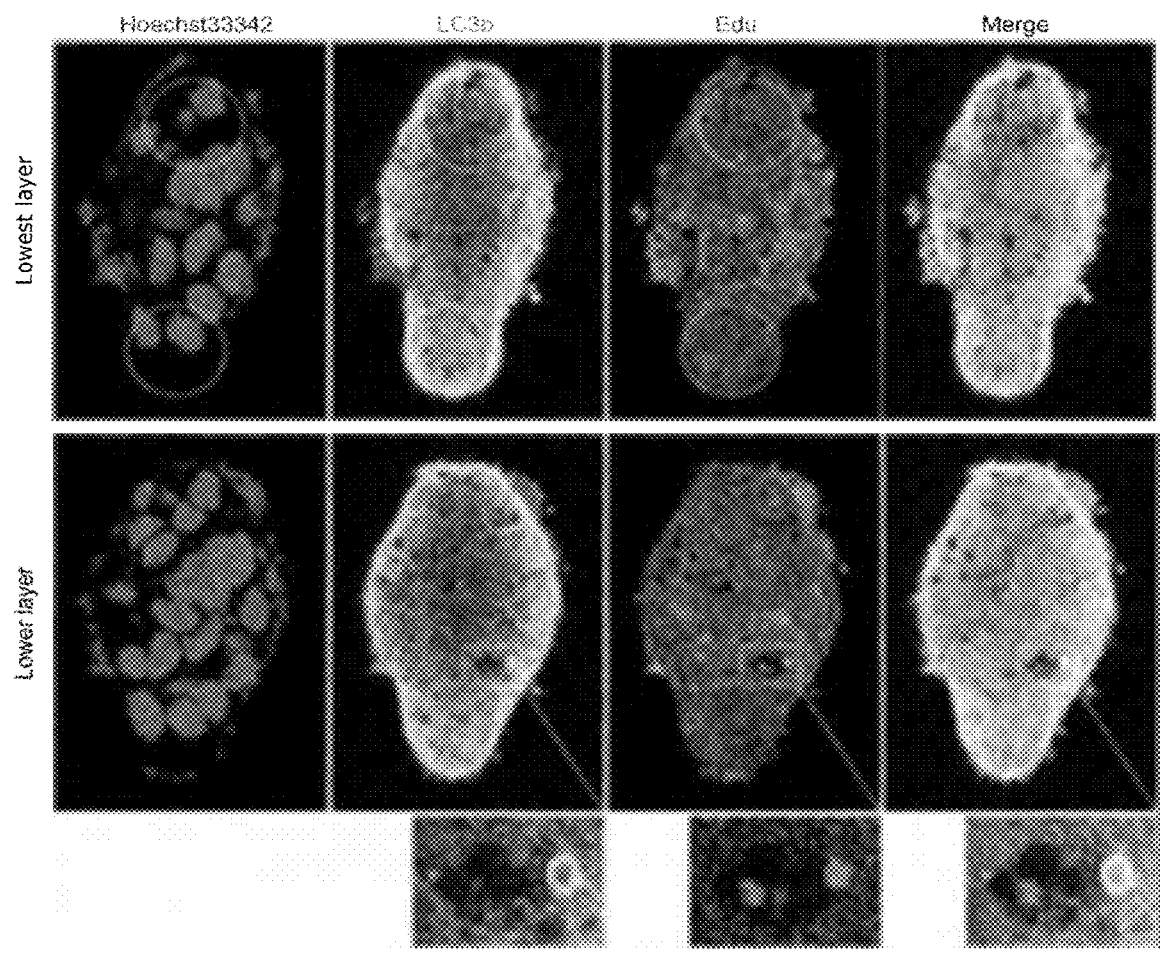
FIG. 45 includes fluorescence images (Hoechst 33342, microtubule-associated protein light chain 3B (LC3B), and EdU; and merger of Hoechst 33342, LC3B, and EdU) of a section of the lower layer of microtumor added with dead cells that have incorporated EdU in the XY direction. In the images, the dotted-line circle indicates the position of a spot.

FIG. 42 to FIG. 44 each illustrate observation images obtained using a fluorescence microscope. A large amount of EdU-positive dead cell debris is accumulated around microtumors (FIG. 42), and a considerable amount of EdU was also detected in the vacuoles of the microtumor (FIG. 43). A part of EdU in the microtumor was detected in lysosome (FIG. 44). Moreover, EdU was also detected in LC3-positive vacuoles, which is the key protein in autophagy (FIG. 45).

Figure 46:
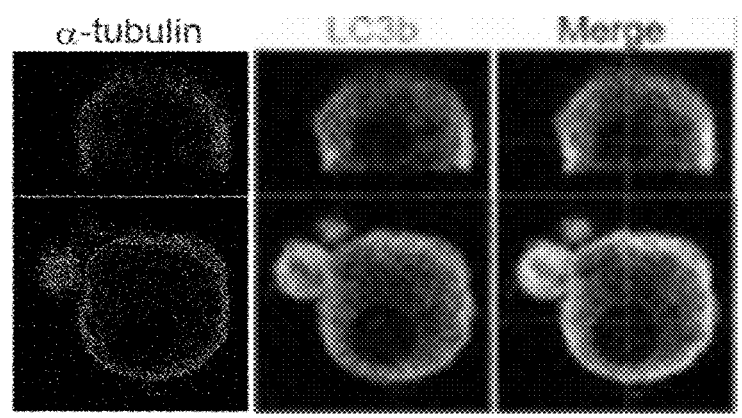
FIG. 46 includes fluorescence images (α-tubulin and LC3B, and merger of α-tubulin and LC3B) of a section of the lower layer of microtumor in the XY direction.
Figure 47:
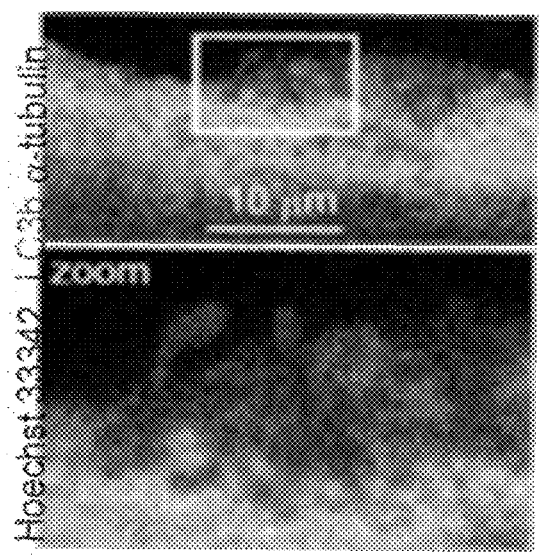
FIG. 47 includes three-dimensional fluorescence images (merger of Hoechst 33342, α-tubulin, and LC3B) of the lower layer of microtumor.

It was also confirmed that LC3 colocalizes with α-tubulin on the surface of microtumor, particularly at the root of cilium on the surface of microtumor (FIG. 46 and FIG. 47).

Given the above, it was confirmed that nucleoside derived from dead cells passes through the surface of microtumor, and a part thereof is localized in the vacuoles of the microtumor and is incorporated in lysosome. It was also confirmed that high expression of LC3 was observed on the surface and in the vacuoles of the microtumor, and the incorporated nucleoside is localized in the LC3-positive vacuoles, in other words, in autophagosome. Enhancement of autophagy and lysosomal catabolism in pancreatic ductal adenocarcinoma have been known. Thus, it was proved that the microtumor is useful as a research model for autophagy and nucleic acid metabolism in the pancreatic ductal adenocarcinoma in vivo.

Example 9

Evaluation of Anticancer Agent Using Microtumors

Figure 48:
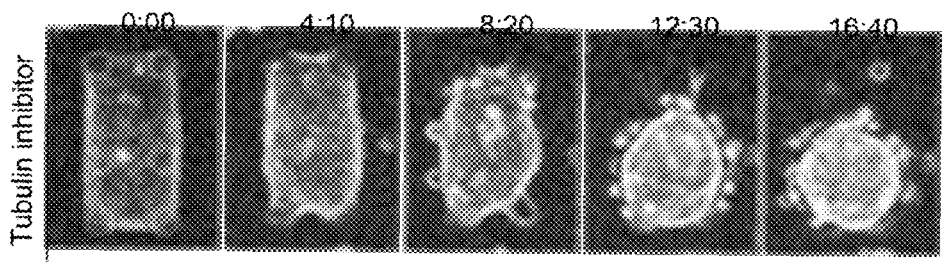
FIG. 48 includes time-lapse DIC images of microtumor treated with a microtubule polymerization inhibitor, nocodazole. In the images, the dotted-line circle indicates the position of a spot.
Figure 49:
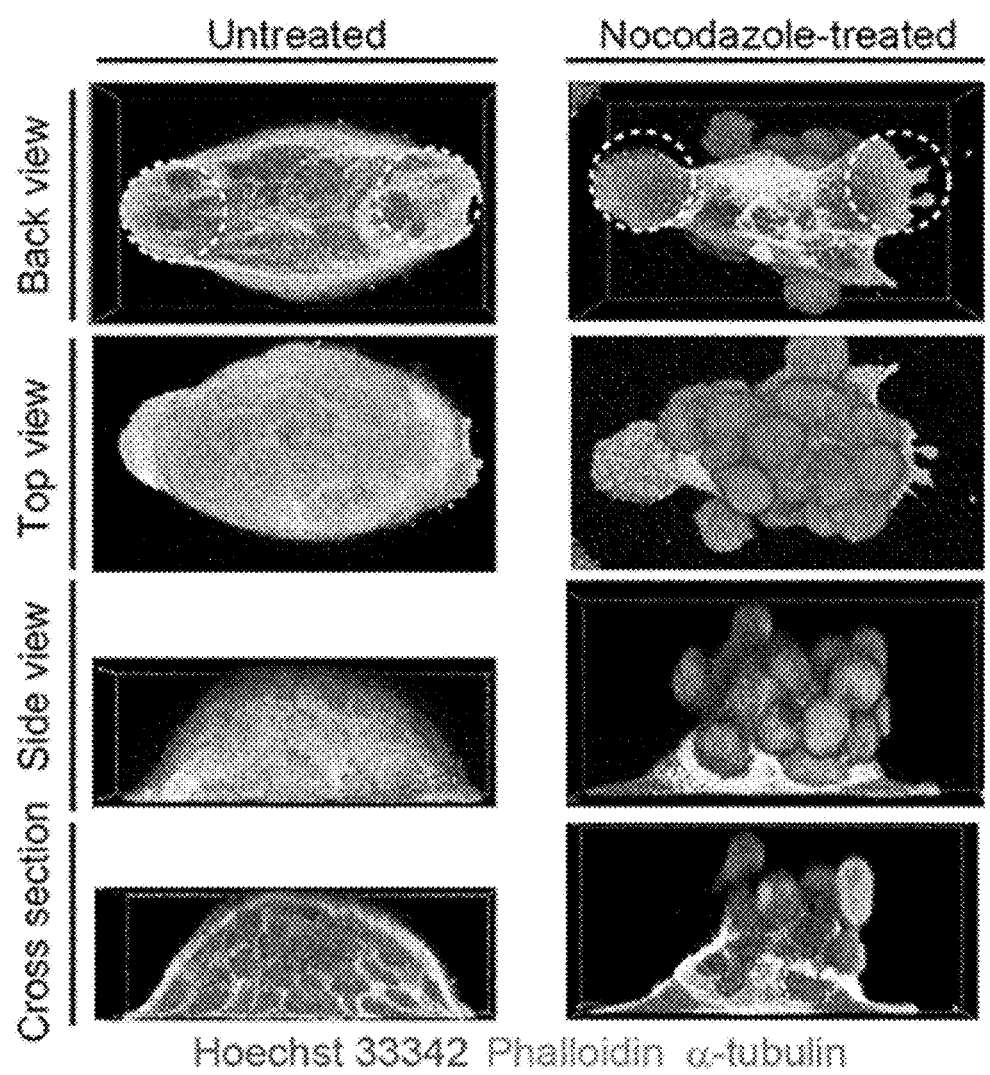
FIG. 49 includes fluorescence images (merger of Hoechst 33342, phalloidin, and α-tubulin) of the bottom surface, the upper surface, the side surface, and the section of microtumor 24 hours after the nocodazole treatment. In the images, the dotted-line circle indicates the position of a spot.

Morphological change in microtumors was observed, by adding nocodazole known as an anticancer agent with microtubule polymerization inhibitory activity to a culture medium of the microtumor consisting of PCI-55 cells formed on the cell culture substrate 1 in Example 2 so that the final concentration becomes 1 µM. By the nocodazole treatment, the microtumor was prevented from adhering to the spot on the cell culture substrate, and formed spheroidal morphology (FIG. 48). Moreover, the membranous expression of α-tubulin in the microtumor disappeared, the cell-in-cell structure was destructed, and a number of viable cells were scattered so as to overflow from the inner microtumor (FIG. 49).

Figure 50:
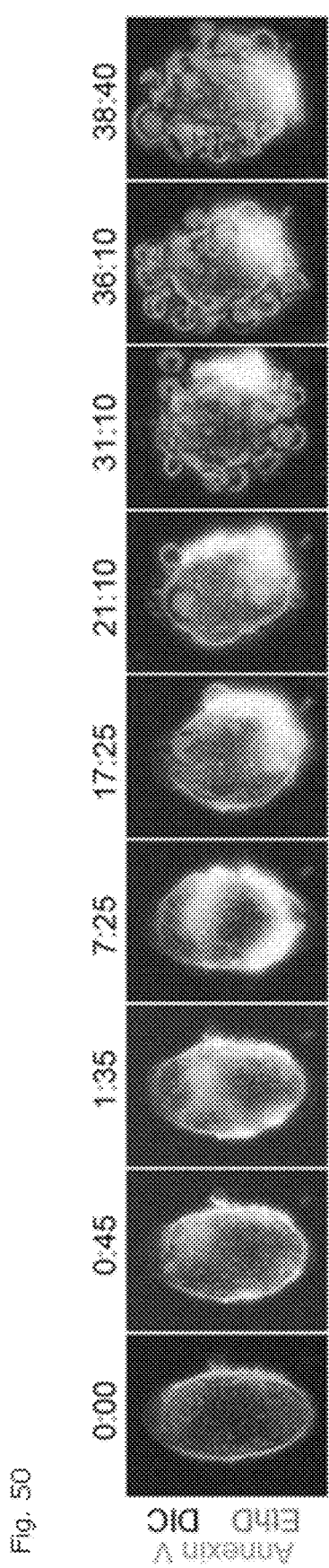
FIG. 50 includes time-lapse images obtained by merging DIC and fluorescence images (Annexin V and EthD) of microtumor treated with nocodazole.

Moreover, paradoxically, the nocodazole treatment reduced the accumulation of Annexin V on the surface of microtumor (FIG. 50), and lost the dead cell phenotype.

Given the above, it was proved that evaluation of anticancer effects of a drug is possible, by using the characteristics of microtumor such as morphology and molecular expression in the drug treatment as an index.

Example 10

Formation of Microtumors on Cell Culture Substrate Having Groove with Uneven Structure on Surface Using the same method as that in Example 1, a cell culture substrate with a pattern in which 166 pieces of straight grooves of 10 µm in width and 10,000 µm in length are arranged per 10 mm$^2$ at 50 µm in interval, and a cell culture substrate with a pattern in which 125 pieces of straight grooves of 30 µm in width and 10,000 µm in length are arranged per 10 mm$^2$ at 50 µm in interval were produced. The grooves in these cell culture substrates have an uneven structure similar to that of the spots in the cell culture substrate 1 on the surface.

Figure 51:
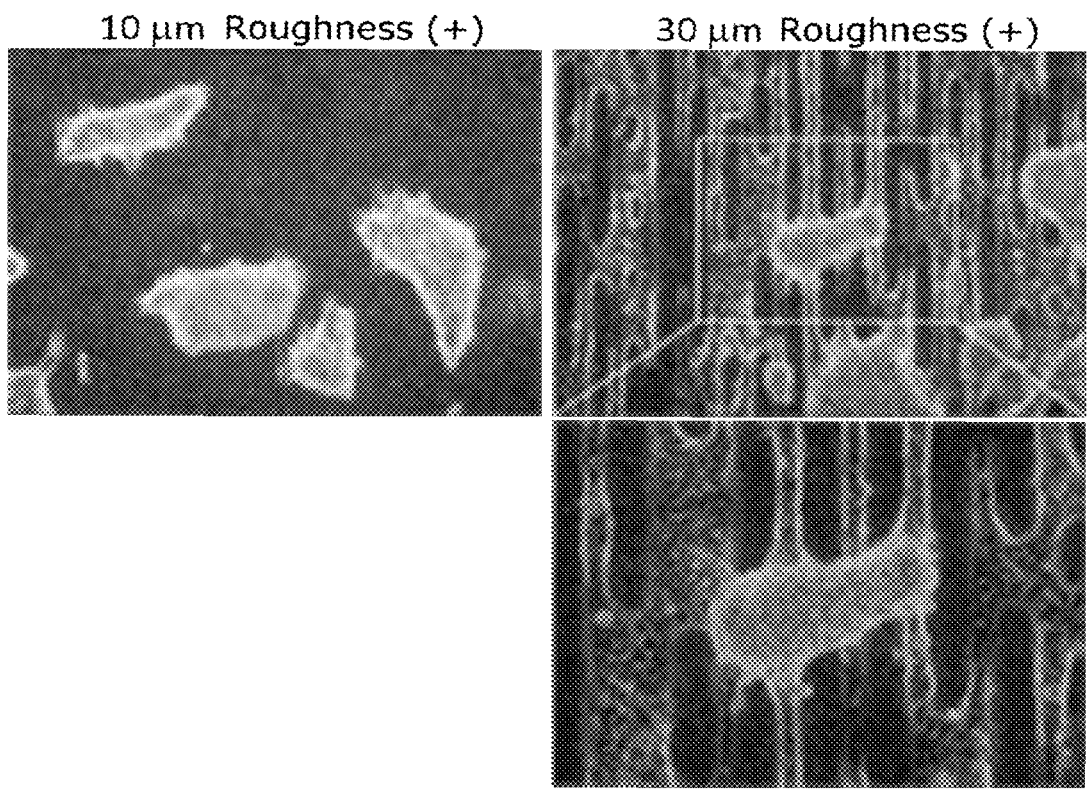
FIG. 51 includes DIC images of PCI-55 cells cultured on a cell culture substrate having a rough section of a groove the width of which is either 10 μm or 30 μm. In the images, the lower right image is an enlargement of a white line frame in the upper right image.

Similar to Example 2, $3 \times 10^6$ of PCI-55 cells suspended in 3 mL of DMEM were seeded on the two types of cell culture substrates described above, and cultured at 37 degrees Celsius overnight to for 48 hours. FIG. 51 is DIC observation images of the cell mass after being cultured. Similar to the cell culture substrate having the rough section of a spot with a diameter ranging from 20 to 100 µm illustrated in Example 2, the formation of a microtumor was also confirmed on the cell culture substrate having a groove the width of which is 10 µm or 30 µm. This microtumor had a number of filipodia along the extending direction of the groove, particularly in the cell culture substrate having a groove the width of which is 10 µm.

Example 11: Evaluation of Anoikis Resistance in Pancreatic Ductal Adenocarcinoma Cells Similar to Example 2, $3 \times 10^6$ of MIA PaCa-2 cells suspended in 3 mL of DMEM were seeded on the cell culture substrate 1, and cultured at 37 degrees Celsius overnight to for 48 hours. While PCI-55 is a human pancreatic ductal adenocarcinoma cell line that has not undergone EMT, that maintained the epithelial phenotype, and that does not have anoikis resistance, MIA PaCa-2 is a human pancreatic ductal adenocarcinoma cell line that has undergone EMT, that has acquired a mesenchymal phenotype, and that has anoikis resistance (cellbank.nibiohn.go.jp/—cellbank/cgi-bin/search res det.cgi?ID=245).

Figure 52:
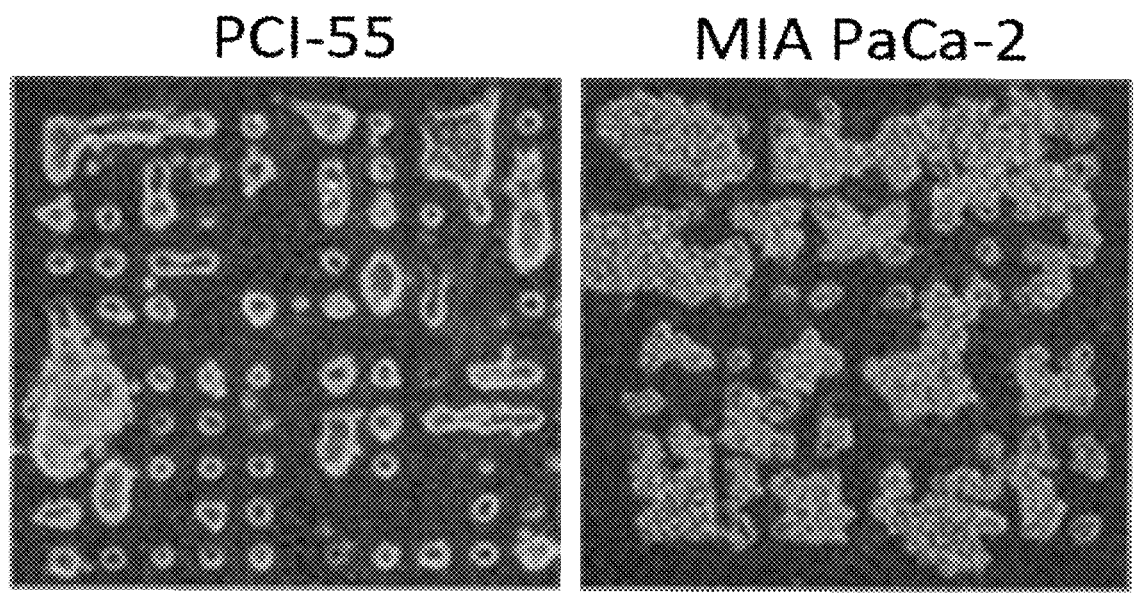
FIG. 52 includes DIC images of PCI-55 cells of an epithelial phenotype and MIA PaCa-2 cells of a mesenchymal phenotype cultured on the cell culture substrate 1.
Figure 53:
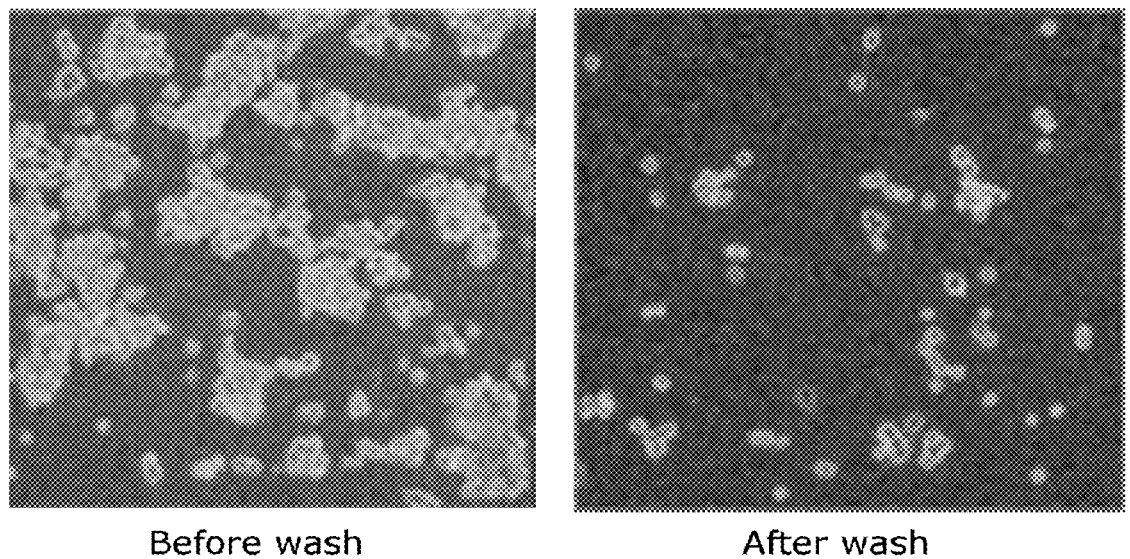
FIG. 53 includes DIC images of live MIA PaCa-2 cells cultured on the cell culture substrate 1 before and after being washed.

FIG. 52 is DIC observation images of cells after being cultured. While PCI-55 cells cultured under the same conditions as MIA PaCa-2 cells have adhered to the substrate and formed a microtumor (left in FIG. 52), MIA PaCa-2 cells that are an adherent cell line of pancreatic ductal adenocarcinoma widely used worldwide did not adhere to the substrate and proliferated while floating in the culture medium (right in FIG. 52). When the cell culture substrate 1 was washed after culturing MIA PaCa-2 cells, most of the cells were removed from the substrate (FIG. 53).

Figure 54:
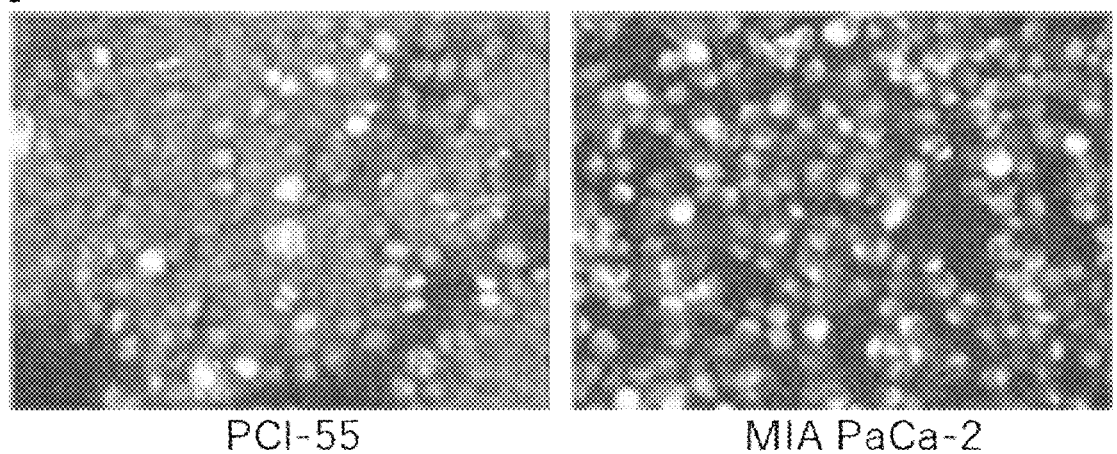
FIG. 54 includes fluorescent images of PCI-55 cells of an epithelial phenotype and MIA PaCa-2 cells of a mesenchymal phenotype cultured on a general cell culture substrate, immunostained with anti-Ki67 antibody.

On the other hand, when PCI-55 cells and MIA PaCa-2 cells were cultured overnight using a polystyrene cell culture substrate (tissue culture flask (traditional type) 25 mL, FALCON) generally used for culturing cells, both of the cells adhered to the substrate and proliferated. The difference in adhesiveness and proliferation was not observed (FIG. 54).

Given the above, the cell culture substrate with a rough section having an uneven structure on the surface can be utilized as a tool for determining the malignancy of cancer cells such as whether epithelial cancer cells have acquired anoikis resistance, whether the cells have undergone EMT and acquired a mesenchymal phenotype, and whether the cells have infiltrative and metastatic potential.

The invention claimed is:

1. A cell culture substrate, comprising:
a base material having a plurality of rough sections; and
a biocompatible polymer layer covering the base material such that the plurality of rough sections is exposed on a surface of the cell culture substrate,
wherein
each of the rough sections has a shape of a spot with a diameter ranging from 20 μm to 100 μm, or a groove with a width ranging from 3 μm to 30 μm, when the shape of the rough section is a groove, an end part of the rough section is optionally connected to another rough section,
a distance between two adjacent rough sections is at least 10 μm or more, and the rough section has at least one uneven structure with a height ranging from 20 nm to 200 nm on the surface.

2. The cell culture substrate according to claim 1, wherein the rough section has a developed interfacial area ratio (Sdr) of 0.002 or more.

3. The cell culture substrate according to claim 1, wherein the distance between the two adjacent rough sections ranges from 10 to 1,200 μm.

4. The cell culture substrate according to claim 1, wherein the rough section has an arithmetic mean roughness (Ra) of 4 nm or more, a maximum height roughness (Rz) of 30 nm or more, and/or an arithmetic mean peak curvature (Spc) of 300 or more.

5. The cell culture substrate according to claim 1, wherein the biocompatible polymer is an amphiphilic polymer that inhibits non-specific adsorption to a biological material.

6. The cell culture substrate according to claim 5, wherein the amphiphilic polymer is 2-methacryloyloxyethyl phosphorylcholine.

7. The cell culture substrate according to claim 5, wherein the amphiphilic polymer is selected from the group consisting of dimethyl polysiloxane, polyethylene glycol, oligoethylene glycol and 2-methacryloyloxyethyl phosphorylcholine.

8. The cell culture substrate according to claim 1, wherein the rough section has an arithmetic mean roughness (Ra) of 4 nm or more.

9. The cell culture substrate according to claim 1, wherein the rough section has a maximum height roughness (Rz) of 30 nm or more.

10. The cell culture substrate according to claim 1, wherein the rough section has an arithmetic mean peak curvature (Spc) of 300 or more.

11. The cell culture substrate according to claim 1, wherein the height of the uneven structure ranges from 30 nm to 100 nm.

12. The cell culture substrate according to claim 1, wherein the height of the uneven structure ranges from 40 nm to 60 nm.

* * * * *